United States Patent
Moore et al.

(10) Patent No.: US 12,367,974 B2
(45) Date of Patent: *Jul. 22, 2025

(54) WOUND THERAPY SYSTEM WITH WOUND VOLUME ESTIMATION

(71) Applicant: Solventum Intellectual Properties Company, Maplewood, MN (US)

(72) Inventors: Brett L. Moore, San Antonio, TX (US); Shannon C. Ingram, Bulverde, TX (US); Justin Rice, Denver, CO (US)

(73) Assignee: Solventum Intellectual Properties Company, Maplewood, MN (US)

( * ) Notice: Subject to any disclaimer, the term of this patent is extended or adjusted under 35 U.S.C. 154(b) by 315 days.

This patent is subject to a terminal disclaimer.

(21) Appl. No.: 17/873,877

(22) Filed: Jul. 26, 2022

(65) Prior Publication Data
US 2022/0362454 A1    Nov. 17, 2022

Related U.S. Application Data

(63) Continuation of application No. 16/366,407, filed on Mar. 27, 2019, now Pat. No. 11,426,506.

(51) Int. Cl.
*A61M 1/00*     (2006.01)
*G16H 40/63*    (2018.01)
*G16H 50/50*    (2018.01)

(52) U.S. Cl.
CPC ............ *G16H 40/63* (2018.01); *A61M 1/73* (2021.05); *A61M 1/742* (2021.05); *A61M 1/77* (2021.05);
(Continued)

(58) Field of Classification Search
CPC .......... A61M 1/73; A61M 1/742; A61M 1/77; A61M 1/85; A61M 1/92; A61M 1/96;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Kai H Weng

(57) ABSTRACT

A wound therapy system includes a negative pressure circuit, a pump, a pressure sensor, and a controller. The negative pressure circuit applies negative pressure to a wound. The pump is fluidly coupled to the negative pressure circuit and produces a negative pressure at the wound or within the negative pressure circuit. The pressure sensor measures the negative pressure within the negative pressure circuit or the wound. The controller performs a testing procedure including a first drawdown period, a leak rate determination period, a vent period, and a second drawdown period. The controller is configured to receive one or more pressure measurements of the pressure sensor over the leak rate determination period to determine a leak rate parameter, monitor an amount of elapsed time over the second drawdown period to determine a drawdown parameter, and estimate a volume of the wound based on the leak rate parameter and the drawdown parameter.

13 Claims, 12 Drawing Sheets

(52) U.S. Cl.
CPC ............... *A61M 1/85* (2021.05); *A61M 1/92* (2021.05); *A61M 1/96* (2021.05); *G16H 50/50* (2018.01); *A61M 2205/15* (2013.01); *A61M 2205/3344* (2013.01); *A61M 2205/3379* (2013.01); *A61M 2205/50* (2013.01); *A61M 2205/702* (2013.01); *A61M 2205/7536* (2013.01)

(58) Field of Classification Search
CPC .............. A61M 1/982; A61M 2205/15; A61M 2205/3344; A61M 2205/3379; A61M 2205/50; A61M 2205/702; A61M 2205/7536; G16H 20/30; G16H 40/63; G16H 50/20; G16H 50/50
See application file for complete search history.

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 7,862,339 | B2 * | 1/2011 | Mulligan ............... A61M 27/00 434/268 |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 10,188,581 | B2 * | 1/2019 | Smith ................... A61M 1/743 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2014/0163491 | A1 | 6/2014 | Schuessler et al. |
| 2015/0080788 | A1 | 3/2015 | Blott et al. |
| 2016/0166740 | A1 | 6/2016 | Hartwell |
| 2017/0165405 | A1 * | 6/2017 | Muser ................... A61F 13/05 |
| 2018/0264181 | A1 * | 9/2018 | Gregory ................ A61M 1/73 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |

(56) References Cited

FOREIGN PATENT DOCUMENTS

| | | |
|---|---|---|
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3372256 A1 | 9/2018 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2009071924 A1 | 6/2009 |
| WO | 2013116158 A2 | 8/2013 |
| WO | 2019023311 A1 | 1/2019 |
| WO | 2019190993 A1 | 10/2019 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinović, V. ? uki?, Ž. Maksimović?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

Japanese Notice of Rejection for Corresponding Application No. 2021-557062, mailed Jan. 31, 2023.

International Search Report and Written Opinion for corresponding application PCT/US2019/024311, dated Dec. 17, 2019.

European Search Report for corresponding application 24207849.1, dated Nov. 12, 2024.

\* cited by examiner

FIG. 9
| | | $\alpha_{time}$ [s] | | | | | |
|---|---|---|---|---|---|---|---|
| | | $\alpha_{time,1}$ | $\alpha_{time,2}$ | $\alpha_{time,3}$ | $\alpha_{time,4}$ | $\alpha_{time,5}$ ... | $\alpha_{time,m}$ |
| $\alpha_{leak}$ [mmHg/s] | $\alpha_{leak,1}$ | $V_{1,1}$ | $V_{1,2}$ | $V_{1,3}$ | $V_{1,4}$ | $V_{1,5}$ ... | $V_{1,m}$ |
| | $\alpha_{leak,2}$ | $V_{2,1}$ | $V_{2,2}$ | $V_{2,3}$ | $V_{2,4}$ | $V_{2,5}$ ... | $V_{2,m}$ |
| | ... | ... | ... | ... | ... | ... | ... |
| | $\alpha_{leak,n}$ | $V_{n,1}$ | $V_{n,2}$ | $V_{n,3}$ | $V_{n,4}$ | $V_{n,5}$ ... | $V_{n,m}$ |
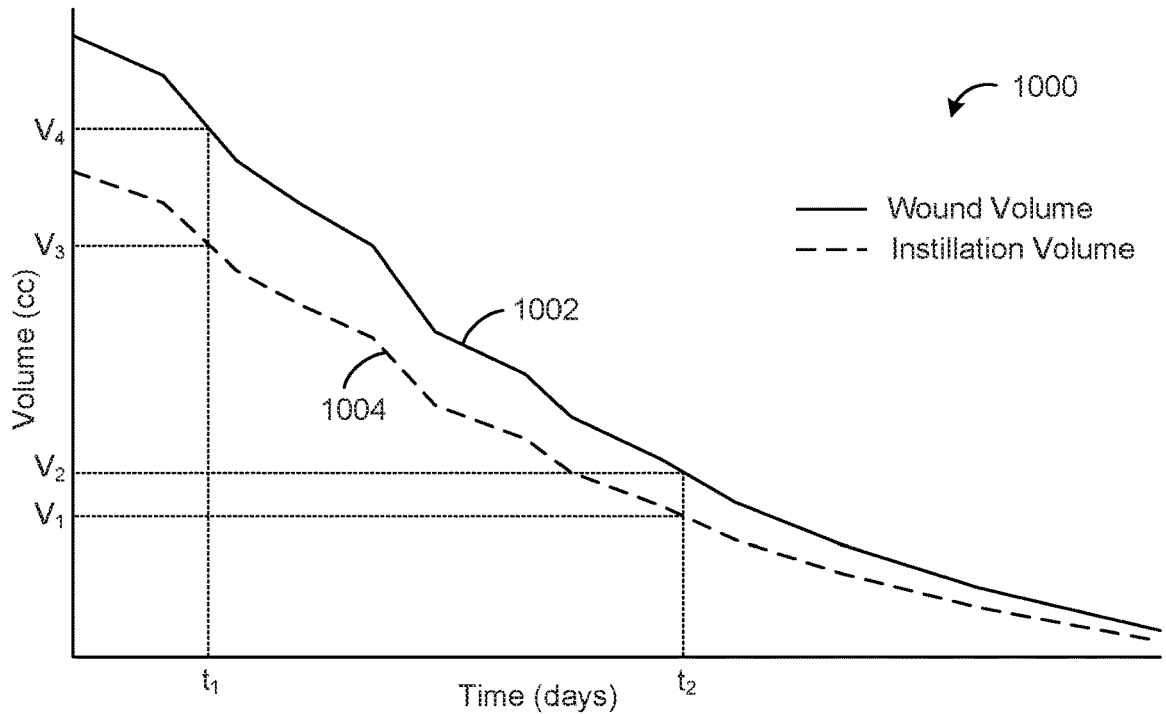
FIG. 10
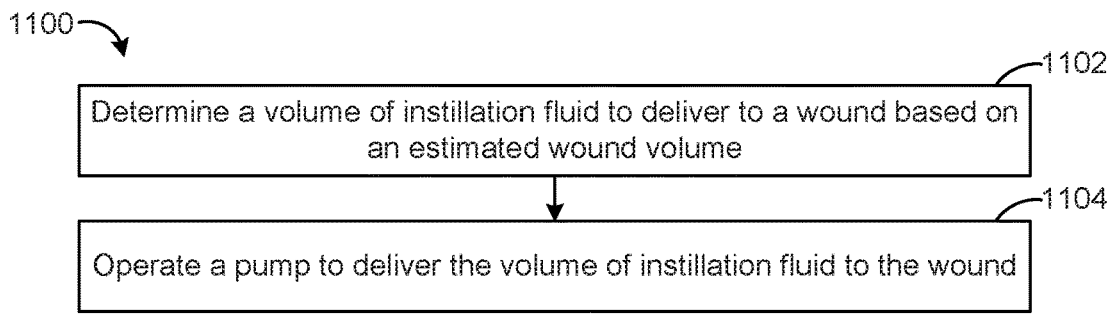
FIG. 11

WOUND THERAPY SYSTEM WITH WOUND VOLUME ESTIMATION

RELATED APPLICATIONS

This application is a continuation of U.S. patent application Ser. No. 16/366,407, entitled "WOUND THERAPY SYSTEM WITH WOUND VOLUME ESTIMATION" filed Mar. 27, 2019, which is incorporated herein by reference for all purposes.

BACKGROUND

Negative pressure wound therapy (NPWT) is a type of wound therapy that involves applying a negative pressure to a wound site to promote wound healing. Some wound treatment systems apply negative pressure to a wound using a pneumatic pump to generate the negative pressure and flow required. Recent advancements in wound healing with NPWT involve applying topical fluids to wounds to work in combination with NPWT. However, it can be difficult to determine the appropriate volume of instillation fluid to deliver to the wound. Additionally, it can be difficult to accurately monitor and track healing progression over time.

SUMMARY

One implementation of the present disclosure is a wound therapy system, according to some embodiments. In some embodiments, the wound therapy system includes a negative pressure circuit, a pump, a pressure sensor, and a controller. In some embodiments, the negative pressure circuit is configured to apply negative pressure to a wound. In some embodiments, the pump is fluidly coupled to the negative pressure circuit and configured to produce a negative pressure at the wound or within the negative pressure circuit. In some embodiments, the pressure sensor is configured to measure the negative pressure within the negative pressure circuit or at the wound. In some embodiments, the controller is configured to perform a testing procedure including a first drawdown period, a leak rate determination period, a vent period, and a second drawdown period. In some embodiments, the controller is configured to receive one or more pressure measurements of the pressure sensor over the leak rate determination period to determine a leak rate parameter. In some embodiments, the controller is configured to monitor an amount of elapsed time over the second drawdown period to determine a drawdown parameter. In some embodiments, the controller is configured to estimate a volume of the wound based on the leak rate parameter and the drawdown parameter.

In some embodiments, the first drawdown period of the testing procedure includes operating the pump to achieve a predetermined negative pressure within the negative pressure circuit.

In some embodiments, the leak rate determination period of the testing procedure includes maintaining the predetermined negative pressure for a predetermined time duration and receiving pressure measurements from the pressure sensor during the predetermined time duration.

In some embodiments, the leak rate parameter is a change in pressure of the negative pressure circuit over the leak rate determination period.

In some embodiments, the leak rate parameter is a change of pressure with respect to time over at least a portion of the leak rate determination period.

In some embodiments, the vent period of the testing procedure includes opening a valve of the negative pressure circuit to allow the negative pressure circuit to return to atmospheric pressure.

In some embodiments, the second drawdown period of the testing procedure includes operating the pump to produce a negative pressure within the negative pressure circuit at a predetermined rate.

In some embodiments, the drawdown parameter is an amount of time the pump operates at the predetermined rate to achieve a predetermined pressure value within the negative pressure circuit.

In some embodiments, the controller is further configured to estimate the volume of the wound by inputting the drawdown parameter and the leak rate parameter into a model that relates the volume of the wound to the drawdown parameter and the leak rate parameter.

In some embodiments, the model is determined by performing the testing procedure for known values of the volume of the wound, and determining the model based on the known values of the volume of the wound, and the leak rate parameters and drawdown parameters associated with each of the known values of the volume of the wound.

Another implementation of the present disclosure is a method for determining volume of a wound, according to some embodiments. In some embodiments, the method includes providing a negative pressure circuit configured to apply negative pressure to a wound. In some embodiments, the method includes providing a pump fluidly coupled to the negative pressure circuit and configured to produce a negative pressure at the wound or within the negative pressure circuit. In some embodiments, the method includes providing a pressure sensor configured to measure the negative pressure within the negative pressure circuit or at the wound. In some embodiments, the method includes performing a testing procedure for a known value of the volume of the wound. In some embodiments, the testing procedure includes performing a first drawdown over a first drawdown period, performing a leak rate determination over a leak rate determination period, venting the negative pressure circuit, and performing a second drawdown over a second drawdown period. In some embodiments, the method includes receiving one or more pressure measurements of the pressure sensor over the leak rate determination period to determine a leak rate parameter. In some embodiments, the method includes monitoring an amount of elapsed time over the second drawdown period to determine a drawdown parameter. In some embodiments, the method includes generating a model based on the known value of the volume of the wound, the leak rate parameter, and the drawdown parameter. In some embodiments, the model relates the volume of the wound to the leak rate parameter and the drawdown parameter. In some embodiments, the method includes re-performing the steps of performing the testing procedure, receiving the one or more pressure measurements, and monitoring the amount of elapsed time to determine a leak rate parameter and a drawdown parameter for an unknown value of the volume of the wound. In some embodiments, the method further includes estimating the unknown value of the volume of the wound by inputting the leak rate parameter and the drawdown parameter associated with the unknown value of the volume of the wound to the model.

In some embodiments, the first drawdown includes operating the pump to achieve a predetermined negative pressure within the negative pressure circuit. In some embodiments, the leak rate determination includes maintaining the predetermined negative pressure for a predetermined time duration and receiving pressure measurements from the pressure sensor during the predetermined time duration.

In some embodiments, the leak rate parameter is a change in pressure of the negative pressure circuit over the leak rate determination period.

In some embodiments, the leak rate parameter is a rate of change of pressure of the negative pressure circuit with respect to time over at least a portion of the leak rate determination period.

In some embodiments, venting the negative pressure circuit includes opening a valve of the negative pressure circuit to allow the negative pressure circuit to return to atmospheric pressure.

In some embodiments, the second drawdown includes operating the pump to produce a negative pressure within the negative pressure circuit at a predetermined drawdown rate.

In some embodiments, the drawdown parameter is an amount of time the pump operates at the predetermined drawdown rate to achieve a predetermined pressure value within the negative pressure circuit.

In some embodiments, the model is determined by performing the testing procedure for multiple known values of the volume of the wound to determine multiple values of the leak rate parameter and the drawdown parameter. In some embodiments, the model is determined by performing a regression on the values of the volume of the wound and the values of the leak rate parameter and the drawdown parameter.

In some embodiments, the model is a lookup table that relates the leak rate parameter and the drawdown parameter to the volume of the wound.

Another implementation of the present disclosure is a wound therapy device, according to some embodiments. In some embodiments, the wound therapy device includes a pump fluidly coupled to a negative pressure circuit. In some embodiments, the pump is configured to produce a negative pressure at a wound or within the negative pressure circuit. In some embodiments, the negative pressure circuit is configured to apply negative pressure to the wound. In some embodiments, the wound therapy device includes a pressure sensor configured to measure the negative pressure within a negative pressure circuit or at the wound, and a controller. In some embodiments, the controller is configured to operate the pump to produce a negative pressure within the negative pressure circuit, receive one or more pressure measurements of the pressure sensor over a predetermined time period, determine a leakage rate based on the one or more received pressure measurements of the pressure sensor over the predetermined time period, vent the negative pressure circuit to atmospheric pressure, and operate the pump to decrease the pressure within the negative pressure circuit at a predetermined rate. In some embodiments, the controller is configured to monitor an amount of elapsed time that the pump operates at the predetermined rate until a predetermined pressure is achieved within the negative pressure circuit. In some embodiments, the controller is configured to estimate a volume of the wound based on the leakage rate and the amount of elapsed time.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

FIG. 9 is a table having a top header of various drawdown time parameter values, a side header of various leak rate parameters, and values of wound volume corresponding to various combinations of the drawdown time parameters and the leak rate parameters, according to an exemplary embodiment.

FIG. 10 is a graph illustrating wound volume and instillation fluid volume over time, according to an exemplary embodiment.

FIG. 11 is a flowchart of a process for determining an amount of instillation fluid to deliver to a wound based on an estimated wound volume, according to an exemplary embodiment.

DETAILED DESCRIPTION

Overview

Figure 1:
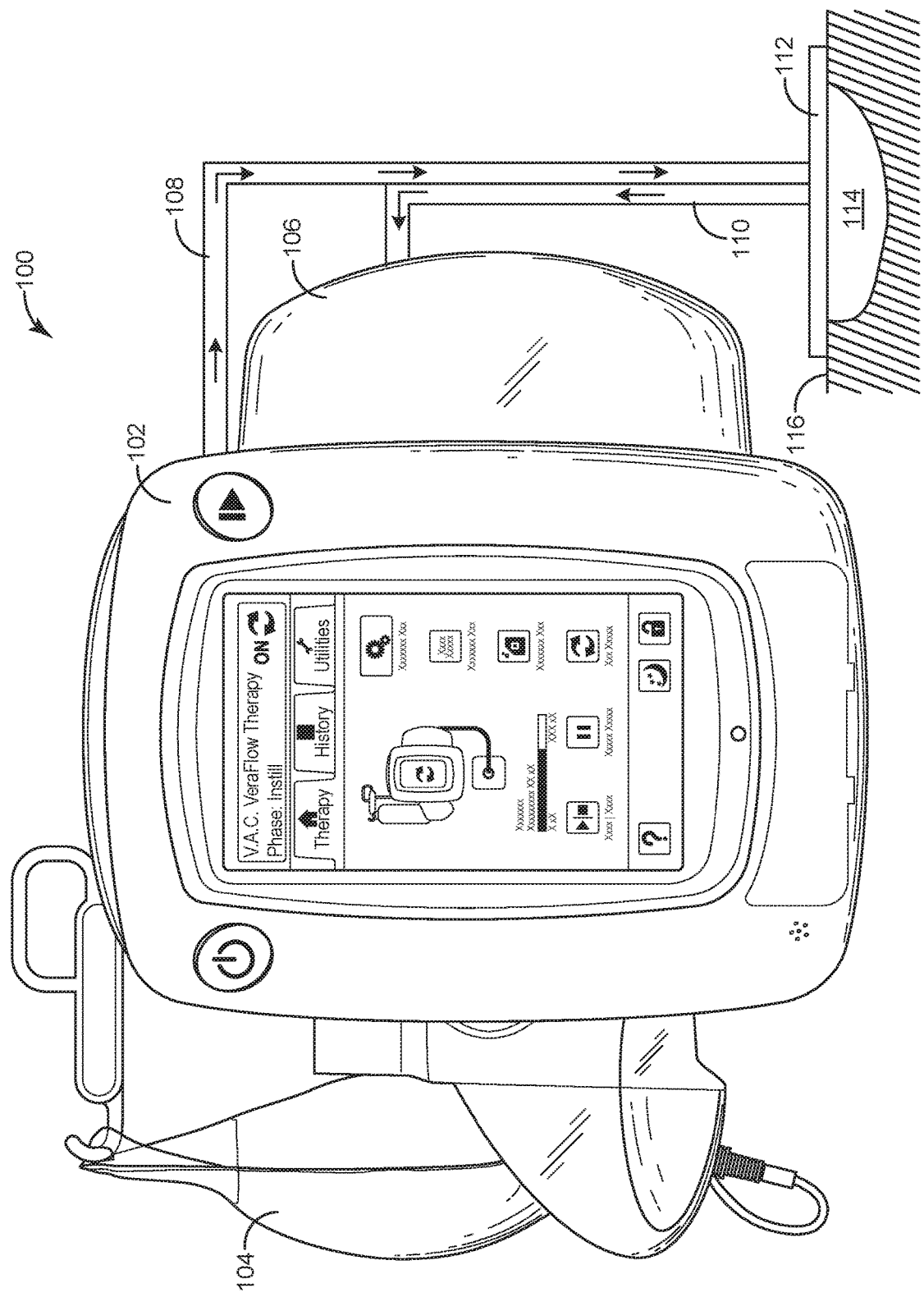
FIG. 1 is a block diagram of a wound therapy system including a therapy device coupled to a wound dressing via tubing, according to an exemplary embodiment.

Referring generally to the FIGURES, a wound therapy system with fluid instillation and removal and components thereof are shown, according to various exemplary embodiments. The wound therapy system may include a therapy device and a wound dressing. The therapy device may include an instillation fluid canister, a removed fluid canister, a valve, a pneumatic pump, an instillation pump, and a controller. The wound dressing can be applied to a patient's skin surrounding a wound. The therapy device can be configured to deliver instillation fluid to the wound and provide negative pressure wound therapy (NPWT) by maintaining the wound at negative pressure. Components of the wound therapy device, the wound dressing, and/or the wound form a negative pressure circuit.

The controller can estimate the volume of the wound based on the leakage rate of the wound dressing and an amount of time it takes the pneumatic pump to achieve a predetermined negative pressure. The controller can cause the therapy device to perform a testing procedure (e.g., a pressure testing procedure) to determine the leakage rate of the wound dressing and the amount of time it takes the pneumatic pump to achieve the predetermined negative pressure. The leakage rate of the wound dressing and the amount of time it takes the pneumatic pump to achieve the predetermined negative pressure at the wound are the observed parameters. For example, the controller can apply the observed parameters as inputs to a model that defines a relationship between the observed parameters and the volume of the negative pressure circuit and/or the volume of the wound. The model may include a polynomial approximation model, a neural network model, or any other model that relates the observed parameters to the volume of the negative pressure circuit and/or the volume of the wound. In some embodiments, the model is a pre-existing model stored in the controller by the manufacturer of the therapy device. In other embodiments, the controller can generate the model on-site by performing a training procedure.

The training procedure may be the same as the pressure testing procedure with the exception that the therapy device is connected to a training circuit having a known volume. For example, the wound dressing can be applied to a test device having a known volume rather than to a patient's skin surrounding a wound. The controller can perform the training procedure on various training circuits having various known volumes and may observe the parameters (i.e., the leakage rate and the amount of time to achieve the predetermined negative pressure) of each training circuit. Each of the known volumes may result in different observed parameters. The controller can then associate the known volume of each training circuit with the corresponding parameters. In some embodiments, the controller uses the observed parameters and the known volume of the training circuits to generate the model that defines a relationship between the observed parameters and the volume of the training circuit. The model can then be stored in the therapy device and used to estimate the volume of a wound, as previously described.

In some embodiments, the controller is configured to execute the pressure testing procedure, observe the parameters, and estimate the wound volume at a plurality of times during wound treatment. The controller can then determine healing progression based on changes in the wound volume during wound treatment. In some embodiments, the controller is configured to determine a volume of instillation fluid to deliver to the wound based on the estimated wound volume. The volume of instillation fluid to deliver may be a predetermined percentage of the volume of the wound (e.g., 20%, 50%, 80%, etc.). The controller can then operate the instillation pump to deliver the determined volume of instillation fluid to the wound. These and other features of the wound therapy system are described in detail below.

Wound Therapy System

Referring now to FIGS. 1-4, a negative pressure wound therapy (NPWT) system 100 is shown, according to an exemplary embodiment. NPWT system 100 is shown to include a therapy device 102 fluidly connected to a wound dressing 112 via tubing 108 and 110. Wound dressing 112 may be adhered or sealed to a patient's skin 116 surrounding a wound 114. Several examples of wound dressings 112 which can be used in combination with NPWT system 100 are described in detail in U.S. Pat. No. 7,651,484 granted Jan. 26, 2010, U.S. Pat. No. 8,394,081 granted Mar. 12, 2013, and U.S. patent application Ser. No. 14/087,418 filed Nov. 22, 2013. The entire disclosure of each of these patents and patent applications is incorporated by reference herein.

Therapy device 102 can be configured to provide negative pressure wound therapy by reducing the pressure at wound 114. Therapy device 102 can draw a vacuum at wound 114 (relative to atmospheric pressure) by removing wound exudate, air, and other fluids from wound 114. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound 114 may include instillation fluid 105 previously delivered to wound 114. Instillation fluid 105 can include, for example, a cleansing fluid, a prescribed fluid, a medicated fluid, an antibiotic fluid, or any other type of fluid which can be delivered to wound 114 during wound treatment. Instillation fluid 105 may be held in an instillation fluid canister 104 and controllably dispensed to wound 114 via instillation fluid tubing 108. In some embodiments, instillation fluid canister 104 is detachable from therapy device 102 to allow canister 106 to be refilled and replaced as needed.

The fluids 107 removed from wound 114 pass through removed fluid tubing 110 and are collected in removed fluid canister 106. Removed fluid canister 106 may be a component of therapy device 102 configured to collect wound exudate and other fluids 107 removed from wound 114. In some embodiments, removed fluid canister 106 is detachable from therapy device 102 to allow canister 106 to be emptied and replaced as needed. A lower portion of canister 106 may be filled with wound exudate and other fluids 107 removed from wound 114, whereas an upper portion of canister 106 may be filled with air. Therapy device 102 can be configured to draw a vacuum within canister 106 by pumping air out of canister 106. The reduced pressure within canister 106 can be translated to wound dressing 112 and wound 114 via tubing 110 such that wound dressing 112 and wound 114 are maintained at the same pressure as canister 106.

Figure 2:
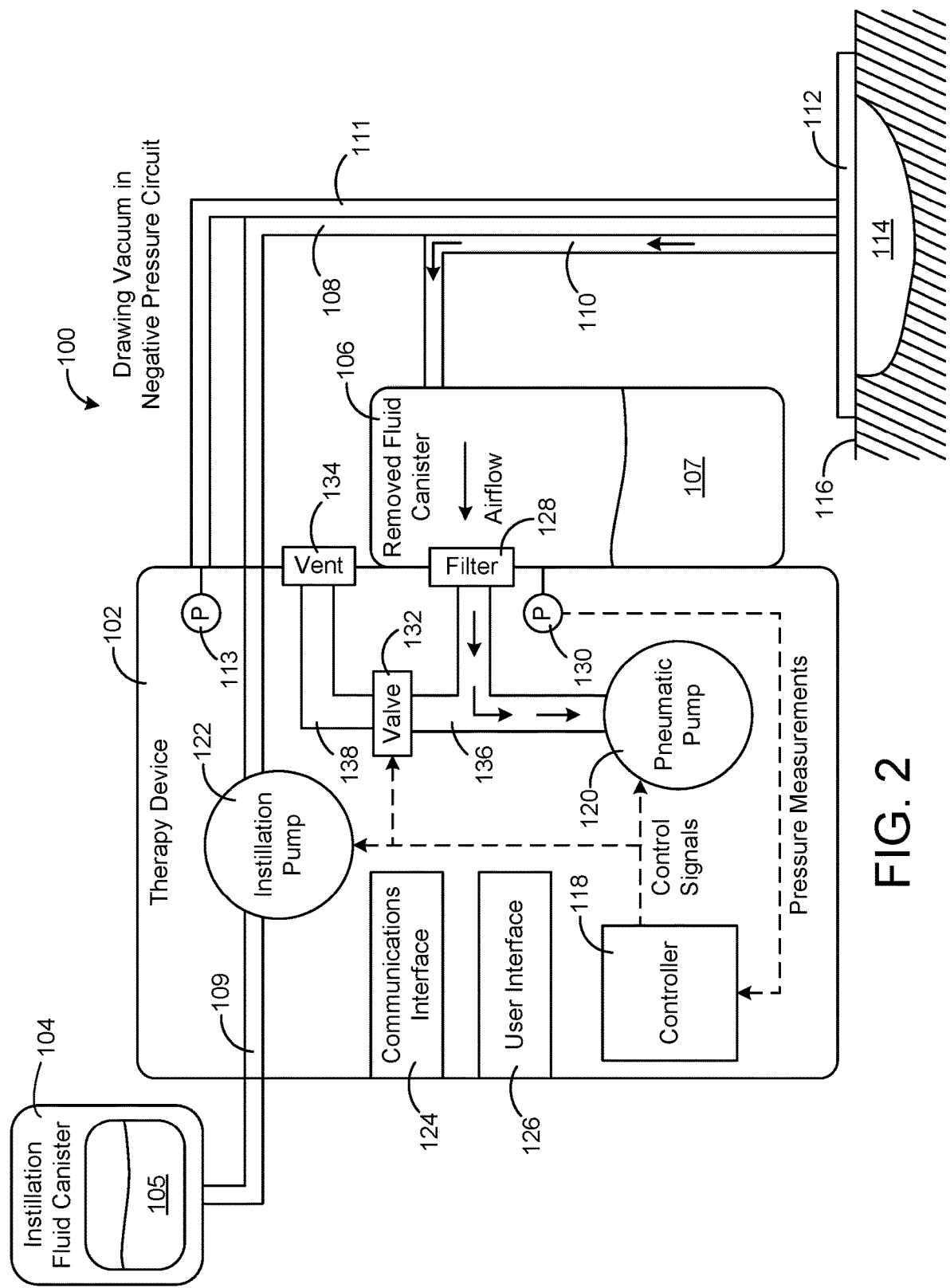
FIG. 2 is a block diagram illustrating the therapy device of FIG. 1 in greater detail when the therapy device operates to draw a vacuum within a negative pressure circuit, according to an exemplary embodiment.
Figure 3A:
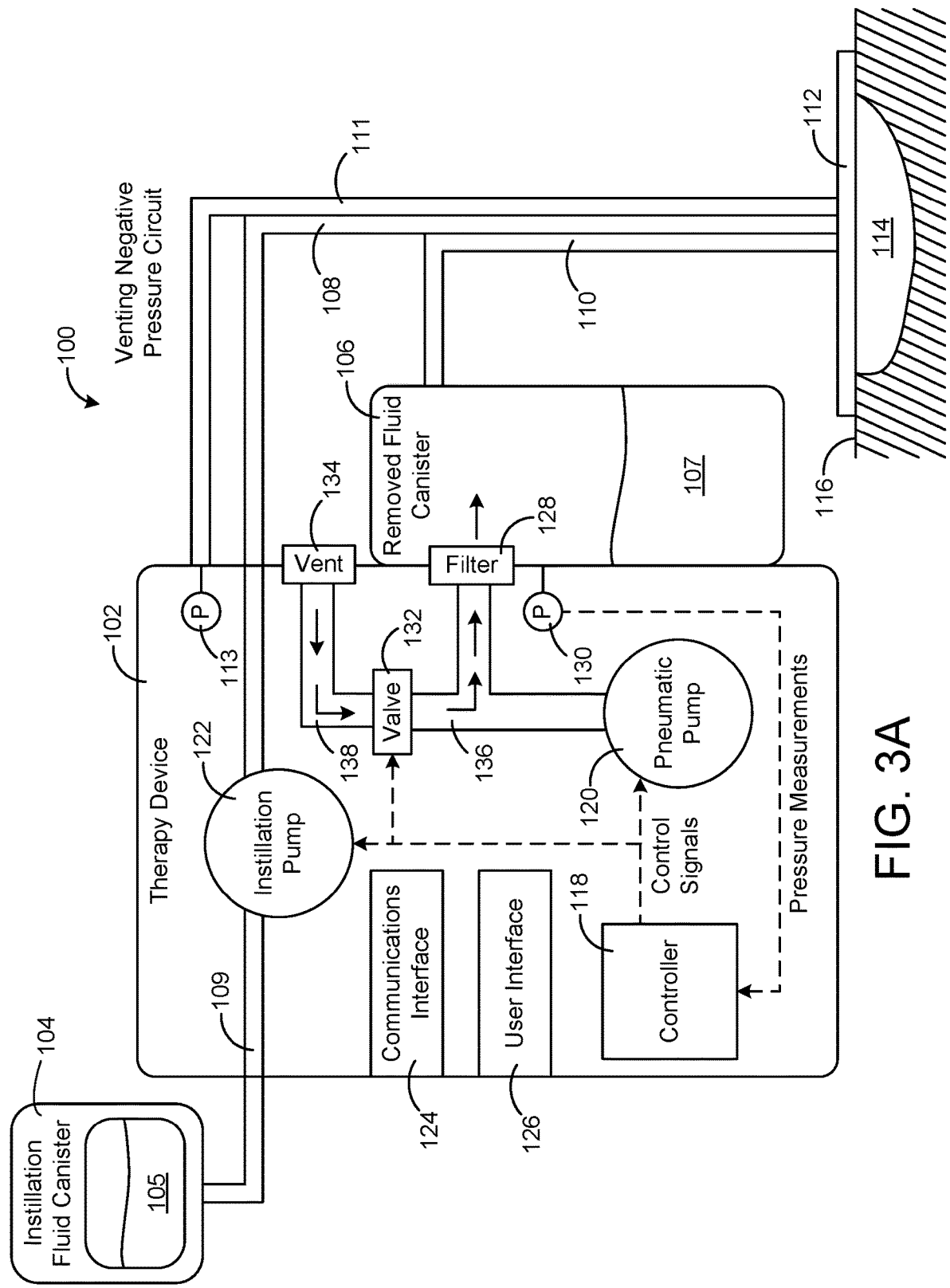
FIG. 3A is a block diagram illustrating the therapy device of FIG. 1 in greater detail when the therapy device operates to vent the negative pressure circuit, according to an exemplary embodiment.
Figure 3B:
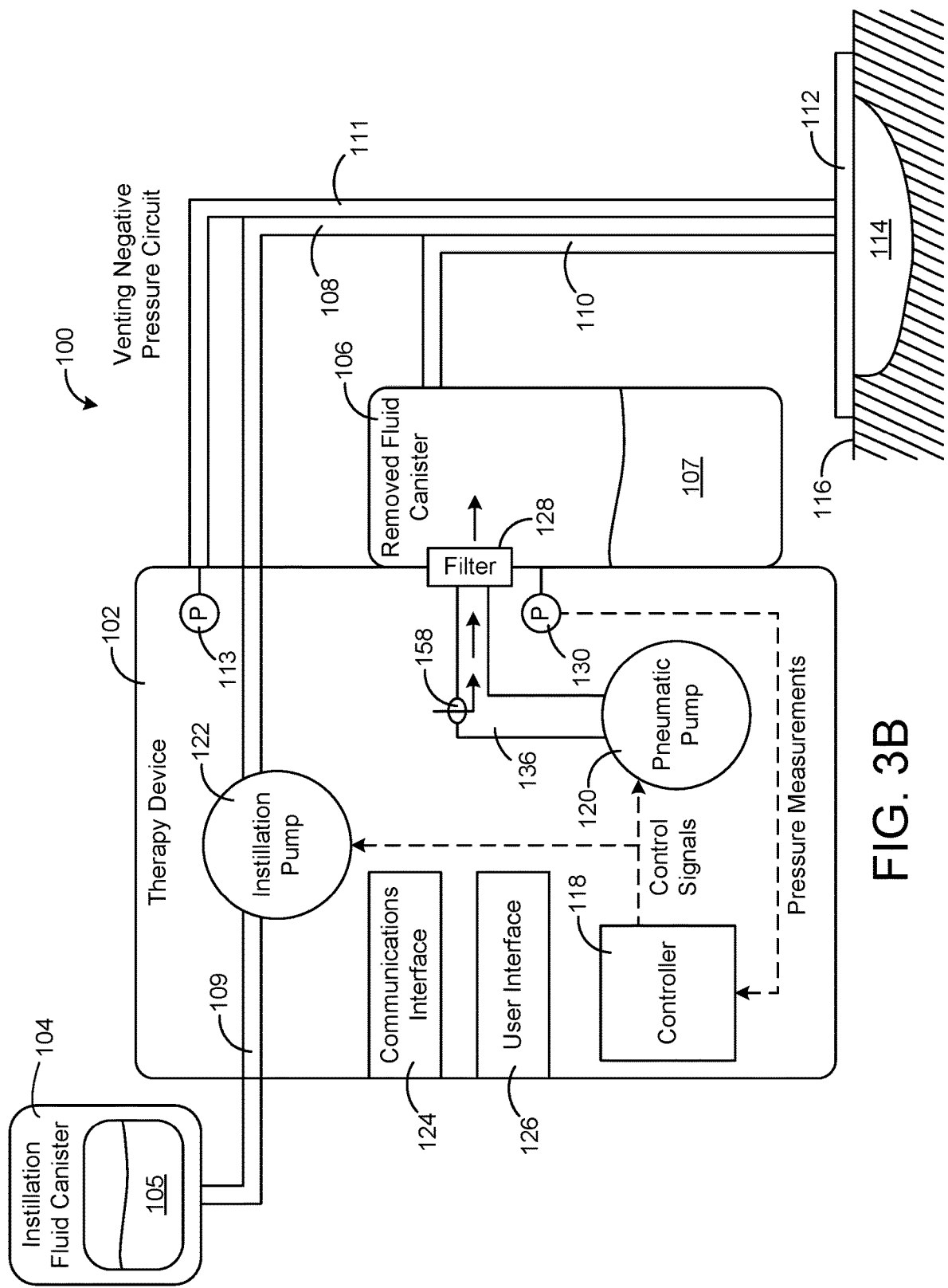
FIG. 3B is a block diagram illustrating the therapy device of FIG. 1 in greater detail when the therapy device uses an orifice to vent the negative pressure circuit, according to an exemplary embodiment.
Figure 4:
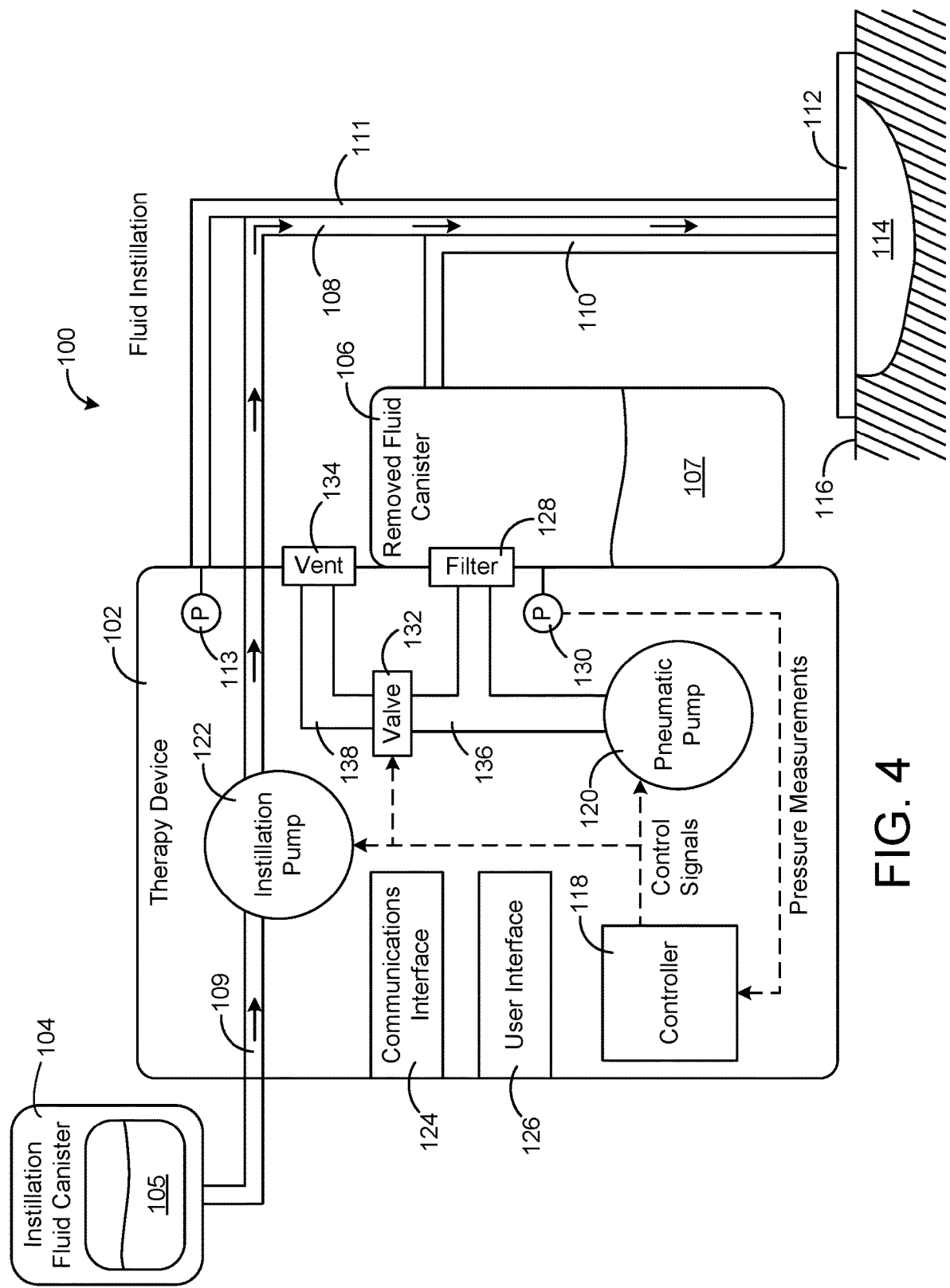
FIG. 4 is a block diagram illustrating the therapy device of FIG. 1 in greater detail when the therapy device operates to deliver instillation fluid to the wound dressing and/or a wound, according to an exemplary embodiment.

Referring particularly to FIGS. 2-4, block diagrams illustrating therapy device 102 in greater detail are shown, according to an exemplary embodiment. Therapy device 102 is shown to include a pneumatic pump 120, an instillation pump 122, a valve 132, a filter 128, and a controller 118. Pneumatic pump 120 can be fluidly coupled to removed fluid canister 106 (e.g., via conduit 136) and can be configured to draw a vacuum within canister 106 by pumping air out of canister 106. In some embodiments, pneumatic pump 120 is configured to operate in both a forward direction and a reverse direction. For example, pneumatic pump 120 can operate in the forward direction to pump air out of canister 106 and decrease the pressure within canister 106. Pneumatic pump 120 can operate in the reverse direction to pump air into canister 106 and increase the pressure within canister 106. Pneumatic pump 120 can be controlled by controller 118, described in greater detail below.

Similarly, instillation pump 122 can be fluidly coupled to instillation fluid canister 104 via tubing 109 and fluidly coupled to wound dressing 112 via tubing 108. Instillation pump 122 can be operated to deliver instillation fluid 105 to wound dressing 112 and wound 114 by pumping instillation fluid 105 through tubing 109 and tubing 108, as shown in FIG. 4. Instillation pump 122 can be controlled by controller 118, described in greater detail below.

Filter 128 can be positioned between removed fluid canister 106 and pneumatic pump 120 (e.g., along conduit 136) such that the air pumped out of canister 106 passes through filter 128. Filter 128 can be configured to prevent liquid or solid particles from entering conduit 136 and reaching pneumatic pump 120. Filter 128 may include, for example, a bacterial filter that is hydrophobic and/or lipophilic such that aqueous and/or oily liquids will bead on the surface of filter 128. Pneumatic pump 120 can be configured to provide sufficient airflow through filter 128 that the pressure drop across filter 128 is not substantial (e.g., such that the pressure drop will not substantially interfere with the application of negative pressure to wound 114 from therapy device 102).

In some embodiments, therapy device 102 operates a valve 132 to controllably vent the negative pressure circuit, as shown in FIG. 3A. Valve 132 can be fluidly connected with pneumatic pump 120 and filter 128 via conduit 136. In some embodiments, valve 132 is configured to control airflow between conduit 136 and the environment around therapy device 102. For example, valve 132 can be opened to allow airflow into conduit 136 via vent 134 and conduit 138, and closed to prevent airflow into conduit 136 via vent 134 and conduit 138. Valve 132 can be opened and closed by controller 118, described in greater detail below. When valve 132 is closed, pneumatic pump 120 can draw a vacuum within a negative pressure circuit by causing airflow through filter 128 in a first direction, as shown in FIG. 2. The negative pressure circuit may include any component of system 100 that can be maintained at a negative pressure when performing negative pressure wound therapy (e.g., conduit 136, removed fluid canister 106, tubing 110, wound dressing 112, and/or wound 114). For example, the negative pressure circuit may include conduit 136, removed fluid canister 106, tubing 110, wound dressing 112, and/or wound 114. When valve 132 is open, airflow from the environment around therapy device 102 may enter conduit 136 via vent 134 and conduit 138 and fill the vacuum within the negative pressure circuit. The airflow from conduit 136 into canister 106 and other volumes within the negative pressure circuit may pass through filter 128 in a second direction, opposite the first direction, as shown in FIG. 3A.

In some embodiments, therapy device 102 vents the negative pressure circuit via an orifice 158, as shown in FIG. 3B. Orifice 158 may be a small opening in conduit 136 or any other component of the negative pressure circuit (e.g., removed fluid canister 106, tubing 110, tubing 111, wound dressing 112, etc.) and may allow air to leak into the negative pressure circuit at a known rate. In some embodiments, therapy device 102 vents the negative pressure circuit via orifice 158 rather than operating valve 132. Valve 132 can be omitted from therapy device 102 for any embodiment in which orifice 158 is included. The rate at which air leaks into the negative pressure circuit via orifice 158 may be substantially constant or may vary as a function of the negative pressure, depending on the geometry of orifice 158. For embodiments in which the leak rate via orifice 158 is variable, controller 118 can use a stored relationship between negative pressure and leak rate to calculate the leak rate via orifice 158 based measurements of the negative pressure. Regardless of whether the leak rate via orifice 158 is substantially constant or variable, the leakage of air into the negative pressure circuit via orifice 158 can be used to generate a pressure decay curve for use in estimating volume 160 (see FIG. 8) of wound 114.

In some embodiments, therapy device 102 includes a variety of sensors. For example, therapy device 102 is shown to include a pressure sensor 130 configured to measure the pressure within canister 106 and/or the pressure at wound dressing 112 or wound 114. In some embodiments, therapy device 102 includes a pressure sensor 113 configured to measure the pressure within tubing 111. Tubing 111 may be connected to wound dressing 112 and may be dedicated to measuring the pressure at wound dressing 112 or wound 114 without having a secondary function such as channeling installation fluid 105 or wound exudate. In various embodiments, tubing 108, 110, and 111 may be physically separate tubes or separate lumens within a single tube that connects therapy device 102 to wound dressing 112. Accordingly, tubing 110 may be described as a negative pressure lumen that functions apply negative pressure wound dressing 112 or wound 114, whereas tubing 111 may be described as a sensing lumen configured to sense the pressure at wound dressing 112 or wound 114. Pressure sensors 130 and 113 can be located within therapy device 102, positioned at any location along tubing 108, 110, and 111, or located at wound dressing 112 in various embodiments. Pressure measurements recorded by pressure sensors 130 and/or 113 can be communicated to controller 118. Controller 118 use the pressure measurements as inputs to various pressure testing operations and control operations performed by controller 118 (described in greater detail with reference to FIGS. 5-14).

Controller 118 can be configured to operate pneumatic pump 120, instillation pump 122, valve 132, and/or other controllable components of therapy device 102. In some embodiments, controller 118 performs a pressure testing procedure by applying a pressure stimulus to the negative pressure circuit. For example, controller 118 may instruct valve 132 to close and operate pneumatic pump 120 to establish negative pressure within the negative pressure circuit. Once the negative pressure has been established, controller 118 may deactivate pneumatic pump 120. Controller 118 may cause valve 132 to open for a predetermined amount of time and then close after the predetermined amount of time has elapsed. Controller 118 may observe a dynamic pressure response of the negative pressure circuit to the pressure stimulus using pressure measurements recorded by pressure sensors 130 and/or 113. The dynamic pressure response may be characterized by a variety of parameters including, for example, a drawdown time parameter $\alpha_{time}$ and a leak rate parameter $\alpha_{leak}$.

Controller 118 can estimate volume 160 of wound 114 based on the observed dynamic pressure response. For example, controller 118 can apply the observed parameters as inputs to a model that defines a relationship between the observed parameters and the volume of the negative pressure circuit and/or volume 160 of wound 114. The model may include a polynomial approximation model, a neural network model, or any other model that relates the observed parameters to the volume of the negative pressure circuit and/or volume 160 of wound 114. In some embodiments, the model is a pre-existing model stored in controller 118 by the manufacturer of therapy device 102. In other embodiments, controller 118 can generate the model on-site by performing a training procedure.

The training procedure may be the same as the pressure testing procedure with the exception that therapy device 102 is connected to a training circuit having a known volume. For example, wound dressing 112 can be applied to a test device having a known volume rather than to a patient's skin 116 surrounding wound 114. Controller 118 can apply the pressure stimulus to various training circuits having various known volumes and may observe the dynamic pressure response of each training circuit. Each of the known volumes may result in a different dynamic pressure response to the pressure stimulus. Controller 118 can then associate the known volume of each training circuit with the corresponding dynamic pressure response. In some embodiments, controller 118 uses the dynamic pressure responses of the training circuits to generate the model that defines a relationship between the observed parameters of the dynamic pressure response (e.g., depth of purge, rebound, delta, leak rate, etc.) and the volume of the training circuit. The model can then be stored in controller 118 and used to estimate the volume of a wound 114, as previously described. In some embodiments, controller 118 determines one or more sets of values of the drawdown time parameter $\alpha_{time}$ and the leak rate parameter $\alpha_{leak}$, where each set of the drawdown time parameter $\alpha_{time}$ and the leak rate parameter $\alpha_{time}$ corresponds to a known volume 160. In some embodiments, controller 118 uses the one or more sets of values to generate the model.

In some embodiments, controller 118 is configured to execute the pressure testing procedure, observe the dynamic pressure response, and estimate volume 160 of wound 114 at a plurality of times during wound treatment. Controller 118 can then determine healing progression based on changes in volume 160 of wound 114 during wound treatment. In some embodiments, controller 118 is configured to determine a volume of instillation fluid 105 to deliver to wound 114 based on the estimated value of volume 160. The volume of instillation fluid 105 to deliver may be a predetermined percentage of volume 160 of wound 114 (e.g., 20%, 50%, 80%, etc.). Controller 118 can then operate instillation pump 122 to deliver the determined volume of instillation fluid 105 to wound 114. These and other features of controller 118 are described in greater detail with reference to FIGS. 5-14.

In some embodiments, therapy device 102 includes a user interface 126. User interface 126 may include one or more buttons, dials, sliders, keys, or other input devices configured to receive input from a user. User interface 126 may also include one or more display devices (e.g., LEDs, LCD displays, etc.), speakers, tactile feedback devices, or other output devices configured to provide information to a user. In some embodiments, the pressure measurements recorded by pressure sensors 130 and/or 113 are presented to a user via user interface 126. User interface 126 can also display alerts generated by controller 118. For example, controller 118 can generate a "no canister" alert if canister 106 is not detected.

In some embodiments, therapy device 102 includes a data communications interface 124 (e.g., a USB port, a wireless transceiver, etc.) configured to receive and transmit data. Communications interface 124 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 124 can include a USB port or an Ethernet card and port for sending and receiving data via an Ethernet-based communications link or network. In another example, communications interface 124 can include a Wi-Fi transceiver for communicating via a wireless communications network or cellular or mobile phone communications transceivers.

Figure 8:
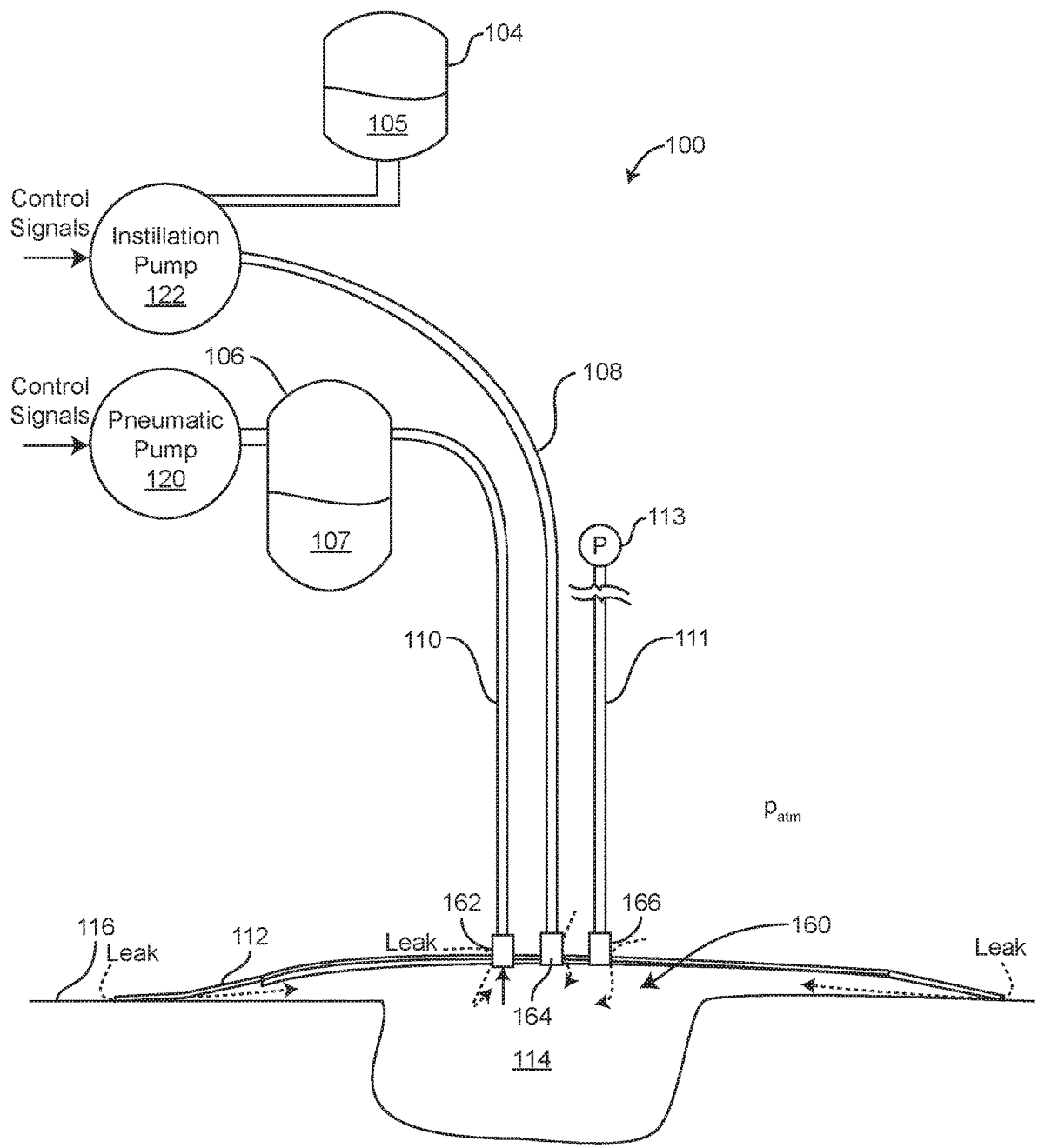
FIG. 8 is a diagram of the wound therapy system of FIG. 1, according to an exemplary embodiment.

Referring now to FIG. 8, wound 114 is shown in greater detail, according to some embodiments. In some embodiments, as the pressure within wound 114 decreases due to operation of pneumatic pump 120, one or more leaks are formed. For example, air may enter volume 160 of wound 114 around corners of wound dressing 112. If tubing 110, 108, and 111 are fluidly coupled with volume 160 via connectors 162, 164, and 166, respectively, a leak can form at connectors 162, 164, and 166. In some embodiments, if the pressure within inner volume 160 of wound 114 (e.g., $p_1$) is less than atmospheric pressure $p_{atm}$ (i.e., the pressure of air outside of wound dressing 112), a pressure differential $\Delta p_{diff} = p_{atm} - p_1$ is formed therebetween. In some embodiments, the pressure differential $\Delta p_{diff}$ causes air to enter volume 160 and travel through tubing 110 via any leaks of wound dressing 112 and connectors 162-166. Leaks may form in any other locations between the interface of wound dressing 112 and a patient's skin 116. In some embodiments, leakages of air into volume 160 of wound 114 is correlated to an increased amount of time which is required for pneumatic pump 120 to achieve a negative pressure.

Controller

Figure 5:
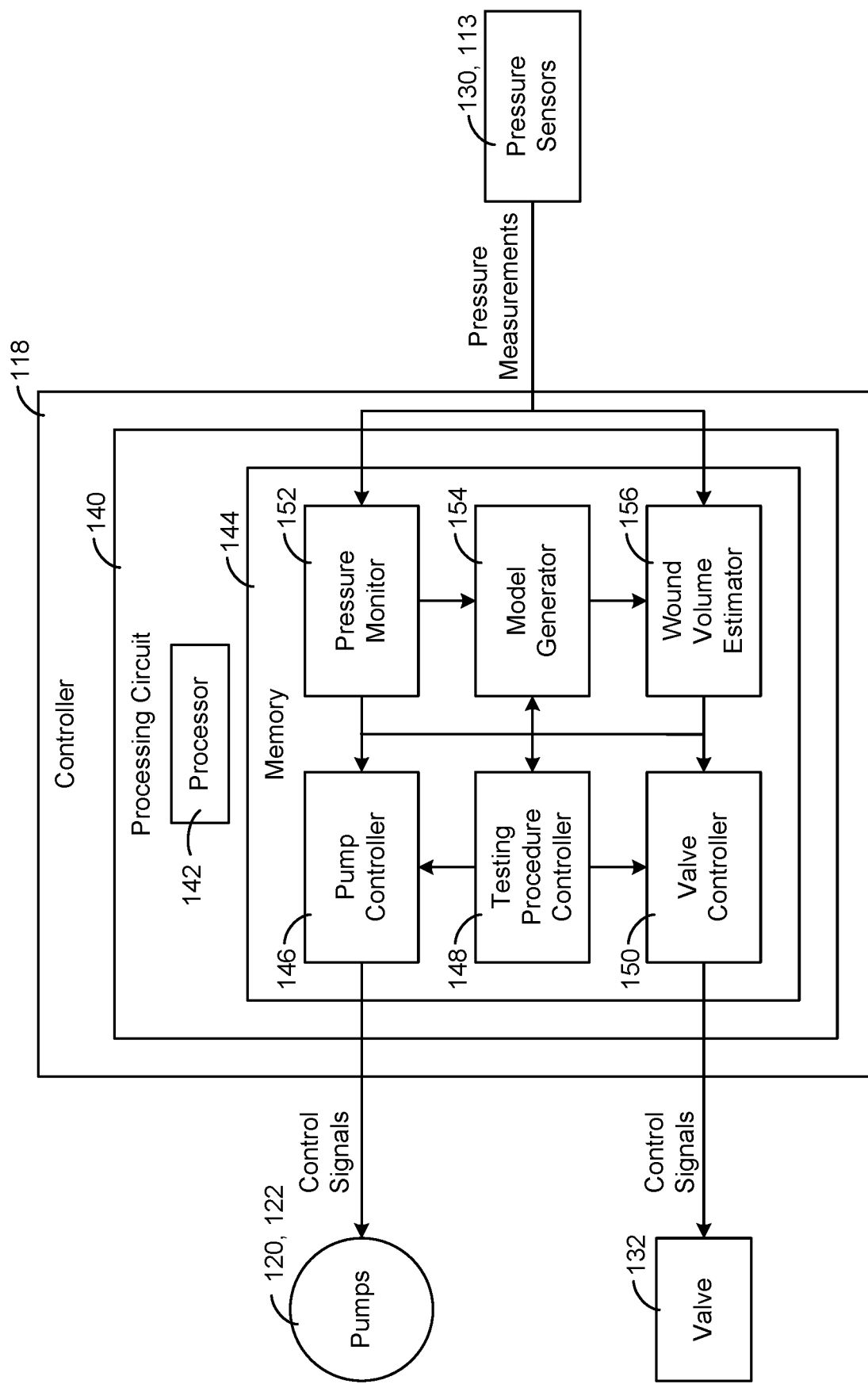
FIG. 5 is a block diagram illustrating a controller of the therapy device of FIG. 1 in greater detail, according to an exemplary embodiment.

Referring now to FIG. 5, a block diagram illustrating controller 118 in greater detail is shown, according to an exemplary embodiment. Controller 118 is shown to include a processing circuit 140 including a processor 142 and memory 144. Processor 142 may be a general purpose or specific purpose processor, an application specific integrated circuit (ASIC), one or more field programmable gate arrays (FPGAs), a group of processing components, or other suitable processing components. Processor 142 is configured to execute computer code or instructions stored in memory 144 or received from other computer readable media (e.g., CDROM, network storage, a remote server, etc.).

Memory 144 may include one or more devices (e.g., memory units, memory devices, storage devices, etc.) for storing data and/or computer code for completing and/or facilitating the various processes described in the present disclosure. Memory 144 may include random access memory (RAM), read-only memory (ROM), hard drive storage, temporary storage, non-volatile memory, flash memory, optical memory, or any other suitable memory for storing software objects and/or computer instructions. Memory 144 may include database components, object code components, script components, or any other type of information structure for supporting the various activities and information structures described in the present disclosure. Memory 144 may be communicably connected to processor 142 via processing circuit 140 and may include computer code for executing (e.g., by processor 142) one or more processes described herein. When processor 142 executes instructions stored in memory 144, processor 142 generally configures controller 118 (and more particularly processing circuit 140) to complete such activities.

Controller 118 is shown to include a pump controller 146 and a valve controller 150. Pump controller 146 can be configured to operate pumps 120 and 122 by generating and providing control signals to pumps 120-122. The control signals provided to pumps 120-122 can cause pumps 120-122 to activate, deactivate, or achieve a variable capacity or speed (e.g., operate at half speed, operate at full speed, etc.). Similarly, valve controller 150 can be configured to operate valve 132 by generating and providing control signals to valve 132. The control signals provided to valve 132 can cause valve 132 to open, close, or achieve a specified intermediate position (e.g., one-third open, half open, etc.). In some embodiments, pump controller 146 and valve controller 150 are used by other components of controller 118 (e.g., testing procedure controller 148, wound volume estimator 156, etc.) to operate pumps 120-122 and valve 132 when carrying out the processes described herein.

In some embodiments, pump controller 146 uses input from a canister sensor configured to detect whether removed fluid canister 106 is present. Pump controller 146 can be configured to activate pneumatic pump 120 only when removed fluid canister 106 is present. For example, pump controller 146 can check whether canister 106 is present and can activate pneumatic pump 120 in response to a determination that canister 106 is present. However, if canister 106 is not present, pump controller 146 may prevent pneumatic pump 120 from activating. Similarly, pump controller 146 can be configured to activate instillation pump 122 only when instillation fluid canister 104 is present. For example, pump controller 146 can check whether canister 104 is present and can activate instillation pump 122 in response to a determination that canister 104 is present. However, if canister 104 is not present, pump controller 146 may prevent instillation pump 122 from activating.

Controller 118 is shown to include a pressure monitor 152. Pressure monitor 152 can be configured to monitor the pressure within removed fluid canister 106 and/or the pressure within wound dressing 112 or wound 114 using feedback from pressure sensors 130 and/or 113. For example, pressure sensors 130 and/or 113 may provide pressure measurements to pressure monitor 152. Pressure monitor 152 can use the pressure measurements to determine the pressure within canister 106 and/or the pressure within wound dressing 112 or wound 114 in real-time. Pressure monitor 152 can provide the pressure value to model generator 154, pump controller 146, testing procedure controller 148, and/or valve controller 150 for use as an input to control processes performed by such components.

Referring now to FIG. 5, controller 118 is shown to include a testing procedure controller 148. Testing procedure controller 148 can be configured to execute a pressure testing procedure to invoke and observe a pressure dynamic response or leakage rate. If therapy device 102 is connected to a wound dressing 112 applied to a patient's skin 116 over a wound 114, testing procedure controller 148 can observe the dynamic pressure response and leakage rate of a negative pressure circuit that includes conduit 136, removed fluid canister 106, tubing 110, wound dressing 112, and/or wound 114 (which may have an unknown volume). If therapy device 102 is connected to a wound dressing 112 applied to a training device having a known volume, testing procedure controller 148 can observe the dynamic pressure response of a training circuit that includes conduit 136, removed fluid canister 106, tubing 110, wound dressing 112, and/or the training device.

Testing Procedure

Figure 6:
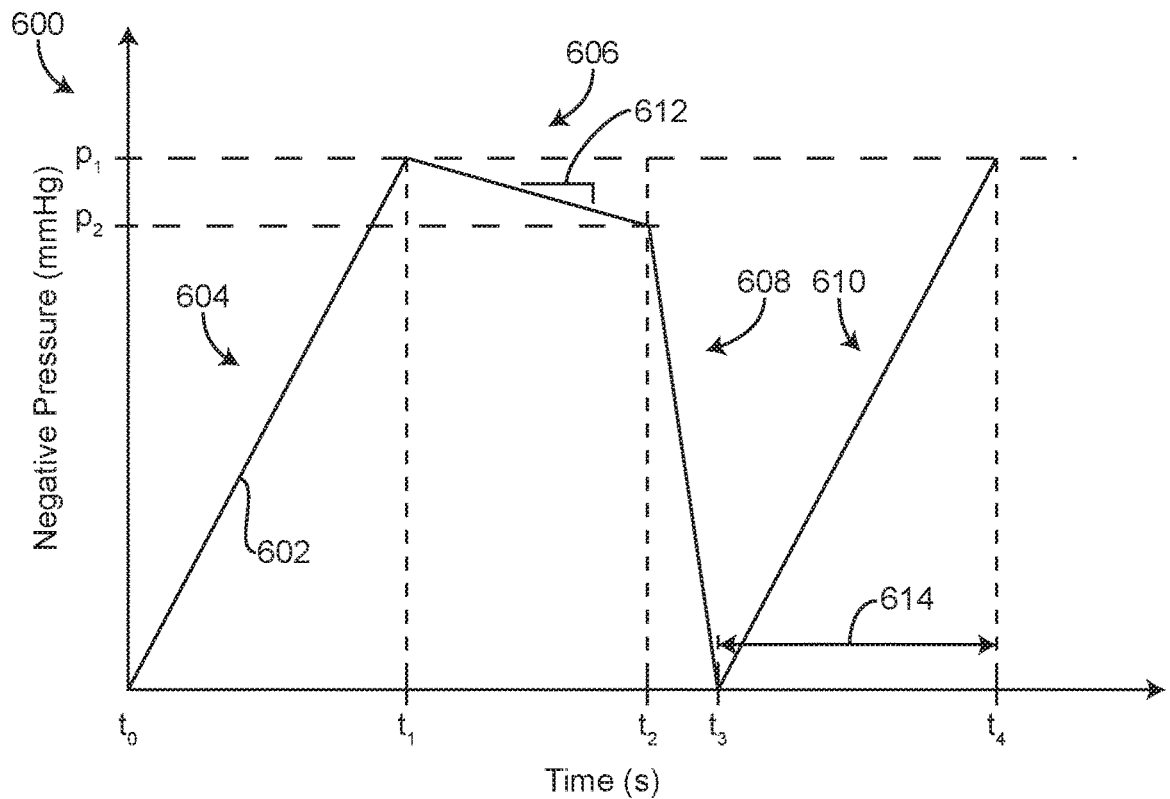
FIGS. 6-7 are graphs illustrating a testing procedure to determine a leak rate parameter and a drawdown time parameter, according to an exemplary embodiment.

Referring particularly to FIG. 6, graph 600 illustrates a testing procedure that controller 118 (e.g., testing procedure controller 148) may be configured to perform, according to some embodiments. In some embodiments, controller 118 is configured to perform the testing procedure shown in graph 600 to determine the leak rate parameter $\alpha_{leak}$ and the drawdown time parameter $\alpha_{time}$.

Graph 600 includes series 602 which shows the relationship between negative pressure (the Y-axis) and time (the X-axis) over the testing procedure, according to some embodiments. In some embodiments, the testing procedure includes a first drawdown period 604, a leak rate determination period 606, a vent period 608, and a second drawdown period 610. In some embodiments, first drawdown period 604 occurs between time $t_0$ and time $t_1$. In some embodiments, leak rate determination period 606 occurs between time $t_1$ and time $t_2$. In some embodiments, vent period 608 occurs between time $t_2$ and time $t_3$. In some embodiments, second drawdown period 610 occurs between time $t_3$ and time $t_4$.

During first drawdown period 604, controller 118 can send a control signal to valve 132 to transition valve 132 into a closed configuration such that air cannot pass through conduit 138 to vent 134. In some embodiments, testing procedure controller 148 sends a command to valve controller 150 to transition valve 132 into a closed configuration for first drawdown period 604. In some embodiments, after valve 132 has been transitioned into the closed configuration, testing procedure controller 148 sends control signals to pump controller 146 to draw down (e.g., create a negative pressure) at wound 114. In some embodiments, testing procedures controller 148 sends information to pump controller 146 regarding a drawdown rate $$\left(\text{i.e., } \frac{\Delta p}{\Delta t}\right).$$

Pump controller 146 is configured to send control signals to pneumatic pump 120 to draw down pressure (e.g., create negative pressure) at wound 114 according to the drawdown rate. In some embodiments, pump controller 146 is configured to operate pneumatic pump 120 to drawdown according to one or more predetermined drawdown rates. In some embodiments, testing procedure controller 148 is configured to send a command to pump controller 146 to cause pneumatic pump 120 to drawdown at a maximum rate for first drawdown period 604. In some embodiments, testing procedure controller 148 sends values of a manipulated variable u to pump controller 146 to cause pneumatic pump 120 to drawdown according to a predetermined drawdown rate. For example, testing procedure controller 148 may send pump controller 146 a binary value of manipulated variable u (e.g., u=1 or u=0). For example, testing procedure controller 148 may send pump controller 146 a value $u_1$=1 of the manipulated variable to pump controller 146 which indicates that pump controller 146 should cause pneumatic pump 120 to drawdown at a first predetermined drawdown rate. Likewise, testing procedure controller 148 may send pump controller 146 a value $u_2$=1 of the manipulated variable to pump controller 146 which indicates that pump controller 146 should cause pneumatic pump 120 to drawdown at a second predetermined drawdown rate which is greater than the first predetermined drawdown rate. Testing procedure controller 148 may send pump controller 146 a 1×d vector of values of the manipulated variable u such as:

$$\vec{u} = [u_1 u_2 \ldots u_d]$$

where $u_1$ is a binary value of the manipulated variable u indicating whether or not pump controller 146 should cause pneumatic pump 120 to drawdown at a first drawdown rate, $u_2$ is another binary value of the manipulated variable u indicating whether or not pump controller 146 should cause pneumatic pump 120 to drawdown at a second drawdown rate, etc., and $u_d$ is a dth binary value of the manipulated variable u indicating whether or not pump controller 146 should cause pneumatic pump 120 to drawdown at a dth drawdown rate. For example, if d=4, and pump controller 146 can cause pneumatic pump 120 to drawdown according to four predetermined drawdown rates, vector $\vec{u}$ may have the form:

$$\vec{u} = [0\ 0\ 0\ 1]$$

such that $u_1=0$, $u_2=0$, $u_3=0$, and $u_4=1$ which indicates that pump controller 146 should cause pneumatic pump 120 to drawdown according to the fourth drawdown rate (i.e., $u_4=1$). In some embodiments, the dth drawdown rate (e.g., in this case, the fourth), is the fastest drawdown rate, while the first drawdown rate is the slowest drawdown rate. In some embodiments, testing procedure controller 148 sends pump controller 146 a command to cause pneumatic pump 120 to drawdown at the fastest drawdown rate for first drawdown period 604 (e.g., $u_d=1$). Testing procedure controller 148 can also use the variable drawdown rate of pneumatic pump for second drawdown period 610. In some embodiments, the drawdown time parameter $\alpha_{time}$ is determined across second drawdown period 610. In some embodiments, if the drawdown rate of pneumatic pump 120 across second drawdown period 610 is fast, the volume estimation of wound 114 is less accurate, but is estimated faster. Likewise, if the drawdown rate of pneumatic pump 120 across second drawdown period 610 is slow, the volume estimation of wound 114 is more accurate, but takes a longer time to estimate. In some embodiments, model generator 154 is configured to determine a model $f_{wound}$ for various predetermined drawdown rates of second drawdown period 610, as described in greater detail below.

In some embodiments, testing procedure controller 148 uses a setpoint value r as a target value of negative pressure for first drawdown period 604. For example, as shown in FIG. 6, $r=p_1$ for first drawdown period 604. In some embodiments, $p_1$ is a low pressure (e.g., a high magnitude of negative pressure) value. In some embodiments, $p_1=200$ mmHg. In some embodiments, $p_1$ is a negative pressure value such that any leaks in wound dressing 112 and/or connectors 162-166 can be monitored. In some embodiments, $p_1$ is a target value of negative pressure to be achieved at wound 114 at the end of first drawdown period 604. For example, as shown in FIG. 6, negative pressure increases throughout first drawdown period 604 until time $t_1$ where $p=p_1$.

In some embodiments, testing procedure controller 148 receives measured pressure values of the pressure p at wound 114 via pressure monitor 152 and pressure sensors 130/113. In some embodiments, testing procedure controller 148 receives values of the pressure p at wound 114 as values of a performance variable y. In some embodiments, testing procedure controller 148 is configured to perform feedback control (e.g., PID control, PI control, etc.) to determine values of the manipulated variable u. In some embodiments, testing procedure controller 148 monitors the values of the performance variable y in real time until the value of the performance variable y is substantially equal to the setpoint value r (e.g., $p_1$). In some embodiments, once the value of the performance variable y is substantially equal to the value of the setpoint r (e.g. $p=p_1$), testing procedure controller 148 sends a value of the manipulated variable u to pump controller 146 to cause pneumatic pump 120 to cease the drawdown. For example, testing procedure controller 148 may initially send pump controller 146 a value of the manipulated variable u such as u=1 until y=r. In some embodiments, once y=r, testing procedure controller 148 sends pump controller 146 a value of the manipulated variable u such as u=0 so that pump controller 146 causes pneumatic pump 120 to stop drawing down pressure p. In some embodiments, once y=r (or once y is within an acceptable range $r\pm r_x$ where $r_x$ indicates an allowable deviation of y from r), testing procedure controller 148 sends a command to pump controller 146 to cease drawing down negative pressure at wound 114.

After first drawdown period has been completed (at $t_1$ as shown in graph 600), leak rate determination period 606 begins, according to some embodiments. Leak rate determination period 606 is used to determine slope 612 which indicates a rate of leakage of the dressing application (e.g., wound dressing 112, connectors 162-166) of wound 114. In some embodiments, slope 612 is the leak rate parameter $\alpha_{leak}$.

During leak rate determination period 606, testing procedure controller 148 causes valve controller 150 to maintain valve 132 in the closed configuration for a predetermined period of time $\Delta t_{leak}$, according to some embodiments. Testing procedure controller 148 monitors pressure changes over leak rate determination period 606 to determine the leak rate parameter $\alpha_{leak}$ for the specific wound application. As shown in graph 600, the negative pressure decreases from $p_1$ to $p_2$ from time $t=t_1$ to time $t=t_2$. In some embodiments, testing procedure controller 148 monitors change in pressure (e.g., a decrease) over leak rate determination period. For example, testing procedure controller 148 can determine a drop in pressure, $p_1-p_2$, over leak rate determination period 606 as the leak rate parameter $\alpha_{leak}$. In some embodiments, leak rate determination period 606 has a predetermined time duration, $\Delta t_{leak}=t_2-t_1$. In some embodiments, testing procedure controller 148 measures pressure $p_1$ at time $t_1$ and pressure $p_2$ at time $t_2$. In some embodiments, the leak rate parameter $\alpha_{leak}=p_1-p_2$ over the predetermined time duration $\Delta t_{leak}$ of leak rate determination period 606.

Leak rate determination period 606 includes testing procedure controller 148 receiving and storing values of the performance variable y (e.g., negative pressure) over the predetermined time period $\Delta t_{leak}$, according to some embodiments. In some embodiments, testing procedure controller 148 receives values of the performance variable y over the predetermined time period $\Delta t_{leak}$ where $\Delta t_{leak}=t_2-t_1$. For example, testing procedure controller 148 may receive values of the performance variable y at a sampling rate $f_{sample}$ over $\Delta t_{leak}$. In some embodiments, the sampling rate is the number of samples of the performance variable y received from pressure sensors 130, 113 in a second, such as $$f_{sample} = \frac{\#\ \text{samples}}{sec}.$$

For example, if testing procedure controller 148 is configured to monitor and record values of the performance variable y from pressure sensors 130, 113 over a ten second interval (i.e., $\Delta t_{leak}=t_2-t_1=10$ seconds), and $f_{sample}=60$ Hz $$\left(\text{i.e.,}\ S_{sample} = 60\frac{\text{samples}}{sec}\right),$$

then the number of samples of the performance variable y over leak rate determination period 606 is $f_{sample} \cdot \Delta t_{leak}$=60 Hz·10 sec=600 samples. In some embodiments, the samples are measured by pressure sensors 130/113, and testing procedure controller 148 records the samples of the performance variable y in a vector, such as: $\vec{S}=[S_1 S_2 \ldots S_w]$ where $S_1$ is the first recorded value of the performance variable y during leak rate determination period 606, $S_2$ is the second recorded value of the performance variable y during leak rate determination period 606, etc., $S_w$ is the wth recorded value of the performance variable y during leak rate determination period 606, and w is the number of samples of the performance variable y over leak rate determination period 606 (e.g., $w=f_{sample} \cdot (t_2-t_1)$).

In some embodiments, testing procedure controller 148 also stores a vector of time values associated with the vector $\vec{S}$. For example, testing procedure controller 148 may store a time vector $\vec{t}=[t_{S_1}, t_{S_2}, \ldots t_{S_w}]$ where $t_{S_1}$ is a time at which $S_1$ is recorded/sampled, $t_{S_2}$ is a time at which $S_2$ is recorded/sampled, etc., and $t_{S_w}$ is a time at which $S_1$ is recorded/sampled. In some embodiments, $t_{S_1}=0$ and $t_{S_w}=(t_2-t_1)$. In some embodiments, $t_{S_1}=t_1$ and $t_{S_w}=t_2$. In some embodiments, each of the values of time vector $\vec{t}$ are spaced apart $$\frac{1}{f_{sample}}.$$

For example, if $f_{sample}$=60 Hz, and $t_{S_1}$ is considered to be 0, $$t_{S_2} = t_{S_1} + \frac{1}{f_{sample}} = 0 + \frac{1}{60} = 0.017 sec.$$

In some embodiments, testing procedure controller 148 is configured to determine slope 612 (i.e., the leak rate parameter $\alpha_{leak}$) based on the vector $\vec{S}$ of samples of the negative pressure at wound 114, and the time vector $\vec{t}$ associated with $\vec{S}$. In some embodiments, testing procedures controller 148 determines slope 612 (i.e., slope m) between consecutive sampling values (e.g., $S_2$ and $S_1$, $S_3$ and $S_2$, $S_4$ and $S_3$, etc.). For example, if testing procedure controller 148 records 5 sampled values (i.e., w=5) over leak rate determination period 606 such that $\vec{S}=[S_1 S_2 S_3 S_4 S_5]$ and $\vec{t}=[t_{S_1} t_{S_2} t_{S_3} t_{S_4} t_{S_5}]$, testing procedure controller 148 determine w−1 values of slope m. For example, testing procedure controller 148 can determine:

$$m_1 = \frac{s_2 - s_1}{t_{S_2} - t_{S_1}}, m_2 = \frac{s_3 - s_2}{t_{S_3} - t_{S_2}}, m_3 = \frac{s_4 - s_3}{t_{S_4} - t_{S_3}}, \text{ and } m_4 = \frac{s_5 - s_4}{t_{S_5} - t_{S_4}}.$$

In some embodiments, testing procedure controller 148 can determine w−1 values of m and store the values in a slope vector such as:

$$\vec{m}=[m_1 m_2 \ldots m_{(w-1)}]$$

where each value of m is determined between consecutively occurring values of S and corresponding/associated values of t at which the samples were recorded.

Testing procedure controller 148 can determine the leak rate parameter $\alpha_{leak}$ based on $\vec{t}$, $\vec{S}$, and $\vec{m}$. In some embodiments, testing procedure controller 148 determines an average of the values of $\vec{m}$ as $\alpha_{leak}$. For example, testing procedure controller 148 can determine:

$$\alpha_{leak} = \overline{m} = \frac{\sum_{i=1}^{w-1} m_i}{w - 1} = \frac{\sum_{i=1}^{w-1} \left( \frac{S_{i+1} - S_i}{t_{S_{i+1}} - t_{S_i}} \right)}{w - 1}$$

according to some embodiments. Testing procedure controller 148 also determines a standard deviation associated with the leak rate parameter $\alpha_{leak}$:

$$\sigma_{leak} = \sqrt{\frac{\sum_{i=1}^{w-1} (m_i - \overline{m})^2}{w - 1}}$$

where:

$$m_i = \left( \frac{S_{i+1} - S_i}{t_{S_{i+1}} - t_{S_i}} \right)$$

according to some embodiments.

In some embodiments, testing procedure controller 148 selects the maximum or minimum value of $\vec{m}$ as $\alpha_{leak}$. For example, testing procedure controller 148 may determine $\alpha_{leak}$ as:

$$\alpha_{leak}=\max(\vec{m})$$

or:

$$\alpha_{leak}=\min(\vec{m})$$

according to some embodiments.

In some embodiments, testing procedure controller 148 uses the initial and final values of $\vec{t}$ and $\vec{S}$ to determine an overall slope m over the entirety of leak rate determination period 606 as the leak rate parameter $\alpha_{leak}$. Testing procedure controller 148 determines:

$$\alpha_{leak} = \frac{S_w - S_1}{t_{S_w} - t_{S_1}} = \frac{p_2 - p_1}{t_2 - t_1}$$

according to some embodiments.

In some embodiments, $\Delta t_{leak}$ (e.g., time between $t_2$ and $t_1$) of leak rate determination period 606 is a predetermined time period. For example $\Delta t_{leak}$ may be 10 seconds, 30 seconds, 5 minutes, etc., according to some embodiments. If $\Delta t_{leak}$ is a predetermined time period, testing procedure controller 148 can determine the leak rate parameter $\alpha_{leak}$ as the change in pressure (e.g., $p_2-p_1$) over the predetermined time period. For example, $\alpha_{leak}=p_2-p_1$ assuming $\Delta t_{leak}$ is a predetermined value. Leak rate determination period 606 is used to determine $\alpha_{leak}$ which characterizes a seal quality at wound 114 and quantifies a leak rate at wound 114. In some embodiments, $\alpha_{leak}$ characterizes an ability of wound 114 to hold a negative pressure. For example, if $\alpha_{leak}$ is very low, this indicates that wound 114 is well sealed and can hold a negative pressure well (e.g., without any leaks) since the pressure drop across leak rate determination period is negligible or slope 612 is a near-zero value. Similarly, if $\alpha_{leak}$ is very high, this indicates that wound 114 is not well sealed and may not hold a negative pressure as well (e.g., identified by a large pressure drop across leak rate determination period 606 or a negative slope 612 with a large magnitude), according to some embodiments.

In some embodiments, after leak rate determination period 606 is completed, testing procedure controller 148 stores the values of $\alpha_{leak}$, $\vec{m}$, $\vec{t}$, and $\vec{S}$ collected/determined over leak rate determination period 606 and proceeds to vent period 608. During vent period 608, testing procedure controller 148 sends a command to valve controller 150 to transition valve 132 into the open configuration to allow wound 114 to return to atmospheric pressure, according to some embodiments. In some embodiments, testing procedure controller 148 causes valve controller 150 to maintain valve 132 in the open configuration for a predetermined amount of time such that the pressure p within wound 114 can return to atmospheric pressure (e.g., 0 mmHg negative pressure). In some embodiments, testing procedure controller 148 monitors the real time value of the performance variable y received from pressure sensors 130/113 via pressure monitor 152 and causes valve controller 150 to maintain valve 132 in the open configuration until the received pressure measurements from pressure sensors 130/113 are substantially equal to atmospheric pressure, as shown at $t_3$.

Figure 7:
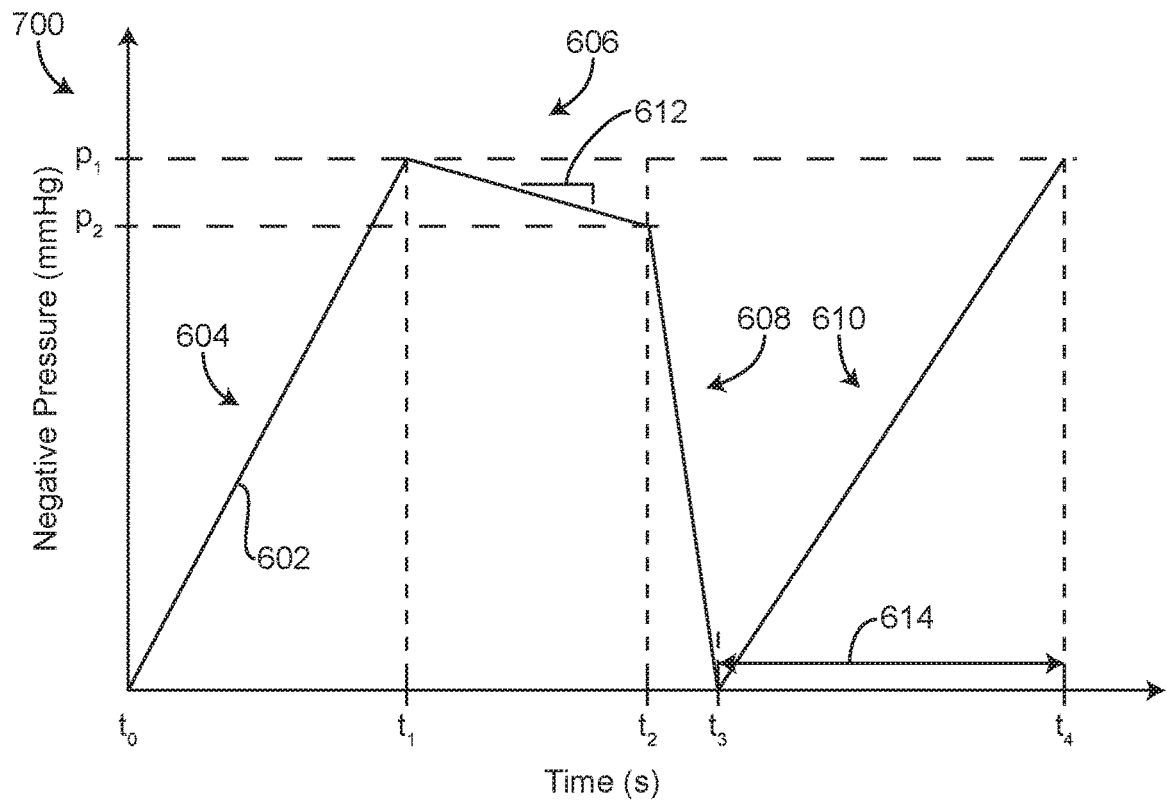

After wound 114 has returned to atmospheric pressure, testing procedure controller 148 proceeds to second drawdown period 610, according to some embodiments. In some embodiments, second drawdown period 610 is performed to determine the drawdown time parameter $\alpha_{time}$. The drawdown time parameter $\alpha_{time}$ is an amount of time required to achieve a desired negative pressure value (e.g., $p_1$). In some embodiments, the drawdown time parameter $\alpha_{time}$ is time interval 614. Time interval 614 as shown in FIG. 17 is greater than time interval 614 as shown in FIG. 16, according to some embodiments. In some embodiments, the value of time interval 614 can increase due to a larger volume of wound 114 and/or a higher leak rate (e.g., a higher value of $\alpha_{leak}$). Slope 612 as shown in FIG. 7 is substantially equal to slope 612 as shown in FIG. 6, according to some embodiments. This may indicate that the wound application (e.g., dressing 112) of the testing procedure as shown in FIG. 6 has a substantially equal leak rate compared to the wound application (e.g., dressing 112) of the testing procedure as shown in FIG. 7. Therefore, the increased value of time interval 614 as shown in FIG. 7, compared to the value of time interval 614 as shown in FIG. 6, may be due to the testing procedure of graph 700 being performed on a wound 114 with a larger volume than wound 114 of the testing procedure of graph 600.

Testing procedure controller 148 can determine the drawdown time parameter $\alpha_{time}$ by sending a command (e.g., a value of the manipulated variable u) to pump controller 146 to cause pneumatic pump 120 to drawdown at a rate of $$\frac{\Delta p}{\Delta t}.$$

Testing procedure controller 148 can receive the pressure measurements from pressure monitor 152 and/or pressure sensors 130/113 and determine an amount of time that pneumatic pump 120 operates to achieve a desired pressure (e.g., $p_1$) as $\alpha_{time}$. In some embodiments, testing procedure controller 148 can send a command to pump controller 146 to cause pneumatic pump 120 to drawdown according to various drawdown rates $$\frac{\Delta p}{\Delta t}.$$

In some embodiments, faster drawdown rates allow $\alpha_{time}$ to be determined quicker but the model determined using $\alpha_{time}$ (described in greater detail below with reference to model generator 154) is less accurate. In some embodiments, slower drawdown rates allow $\alpha_{time}$ to be used to generate a more accurate model, but require longer drawdown time (e.g., time interval 614) to determine $\alpha_{time}$.

In some embodiments, testing procedure controller 148 is configured to send a command to valve controller 150 to transition valve 132 into the closed configuration to initiate second drawdown period 610. In some embodiments, after valve 132 has been transitioned into the closed configuration, testing procedure controller 148 sends a command to pump controller 146 to initiate a second drawdown. In some embodiments, testing procedure controller 148 sends a value of the manipulated variable u to pump controller 146 to cause pneumatic pump 120 to drawdown the negative pressure at wound 114. In some embodiments, testing procedure controller 148 sends a command (e.g., a value of the manipulated variable u) to pump controller 146 to cause pneumatic pump 120 to drawdown according to a predetermined drawdown operation. In some embodiments, the predetermined drawdown operation includes increasing the voltage supplied to pneumatic pump 120 if pneumatic pump 120 cannot achieve the desired negative pressure (e.g., $p_1$) given the current voltage. In some embodiments, the voltage increases of pneumatic pump 120 are performed at predetermined/known time intervals.

Similar to first drawdown period 604, testing procedure controller 148 can send values of the manipulated variable u to pump controller 146 to cause pneumatic pump 120 to drawdown at a variety of drawdown rates for second drawdown period 610. In some embodiments, faster drawdown rates result in a less accurate estimation of the drawdown time parameter $\alpha_{time}$ but can advantageously be used to estimate the drawdown time parameter $\alpha_{time}$ faster. Likewise, slower drawdown rates advantageously result in a more accurate estimation of the drawdown time parameter $\alpha_{time}$ but require a longer amount of time to estimate the drawdown time parameter $\alpha_{time}$, according to some embodiments.

During second drawdown period 610, testing procedure controller 148 monitors the value of the performance variable y received from pressure sensors 130, 113 via pressure monitor 152 and compares the value of the performance variable y to the desired/setpoint value r. In some embodiments, the desired/setpoint value r is a negative pressure value at wound 114 that pneumatic pump 120 is trying to achieve (e.g., a target pressure value). For example, the setpoint value r may be $p_1$. In some embodiments, the setpoint value r is greater than or less than $p_1$. In this way, the target pressure value of second drawdown period 610 may be the same, or greater than, or less than the target pressure value of first drawdown period 604.

Testing procedure controller 148 continues monitoring the value of the performance variable y and monitoring an amount of elapsed time since the beginning (e.g., $t_3$) of second drawdown period 610, according to some embodiments. In some embodiments, testing procedure controller 148 includes a timer configured to reset at the beginning of second drawdown period 610 (e.g., at $t_3$) or to store a time at which second drawdown period 610 begins (e.g., store the value of $t_3$). In some embodiments, the timer resets or records the time value immediately after valve 132 has transitioned into the closed configuration and once pneumatic pump 120 has begun drawing down pressure at wound 114.

In some embodiments, once the value of the performance variable y is substantially equal to the setpoint r (e.g., equal to, within a negligible amount, etc.), the timer of testing procedure controller 148 records time $t_4$. In some embodiments, testing procedure controller 148 monitors the amount of time (i.e., $t_4-t_3$) required to achieve the desired negative pressure value (e.g., r, $p_1$). In some embodiments, testing procedure controller 148 monitors the elapsed time to drawdown to $p_1$ or r. In some embodiments, the amount of elapsed time $\Delta t_{drawdown} = t_4 - t_3$. In some embodiments, the amount of elapsed time $\Delta t_{drawdown}$ is the drawdown time parameter $\alpha_{time}$.

Testing procedure controller 148 can perform the testing procedure as described in greater detail above to determine values of the leak rate parameter $\alpha_{leak}$ and the drawdown time parameter $\alpha_{time}$ for a known volume of wound 114 and/or a known training circuit volume. For example, testing procedure controller 148 can perform the testing procedure multiple times for a variety of several training circuits having known volumes (e.g., 50 cc, 100 cc, 200 cc, 300 cc, etc.). In some embodiments, testing procedure controller 148 is configured to perform the testing procedure several times for each of the training circuits having known volumes. In some embodiments, the resulting values of the leak rate parameter $\alpha_{leak}$ and the drawdown time parameter $\alpha_{time}$ are averaged for each of the training circuits to mitigate an amount of random error. For example, the testing procedure may be performed 10 times for a training circuit having the known volume of 50 cc and the leak rate parameter $\alpha_{leak}$ and the drawdown time parameter $\alpha_{time}$ can be averaged to reduce random error. In some embodiments, the testing procedure is performed for various NPWT systems having different pneumatic pumps 120, therapy pressures, training circuit volumes, etc. In some embodiments, model generator 154 is configured to generate a model for each of multiple training circuits using any of the methods and techniques described in greater detail below.

In some embodiments, the training circuit volume includes known volume values of the various pipes, canisters, tubes, etc., which pneumatic pump 120 is configured to draw down. In some embodiments, the training circuit volume includes a known volume of wound 114, $V_{wound}$. In some embodiments, the training circuit volume is:

$$V_{training} = V_{system} V_{wound}$$

where $V_{system}$, is the known volume of various tubes, pipes, canisters, etc., which pneumatic pump 120 is configured to produce a negative pressure within (e.g., conduit 136, removed fluid canister 106, tubing 110, wound dressing 112, and/or wound 114), and $V_{wound}$ is a known volume of wound 114.

In some embodiments, the testing procedure can be performed multiple times for a variety of values of $V_{wound}$. For example, the testing procedure can be performed by controller 118 for a value of $V_{wound}=50$ cc, $V_{wound}=100$ cc, $V_{wound}=125$ cc, etc. In some embodiments, the testing procedure is performed multiple times for each value of $V_{wound}$ to determine average parameter values associated with the particular value of $V_{wound}$. In some embodiments, $V_{system}$ is held constant while the testing procedure is repeated for various values of $V_{wound}$. In this way, changes in the overall volume of the training circuit, $V_{training}$ are due to changes in $V_{wound}$. The testing procedure can also be performed multiple times for each value of $V_{wound}$ having multiple leak rates. In some embodiments, testing procedure controller 148 is configured to provide model generator 154 with the leak rate parameter $\alpha_{leak}$ and the drawdown time parameter $\alpha_{time}$ for each combination of leak rate and $V_{wound}$ resulting from performing the testing procedure.

In some embodiments, controller 118 performs the testing procedure for various systems having different values of $V_{system}$. In some embodiments, controller 118 performs the testing procedure multiple times for various values of $V_{wound}$ for each of the various systems. In some embodiments, model generator 154 is configured to generate a model for each of the various systems using any of the methods and techniques described in greater detail below. For example, model generator 154 can generate a model for various training circuits which may be used during NPWT.

In some embodiments, model generator 154 is configured to determine a model to relate the recorded/determined parameters (i.e., $\alpha_{leak}$ and $\alpha_{time}$) to $V_{wound}$ for the known values of $V_{wound}$. This model can then be used during NPWT to determine the volume of an unknown wound 114. Model generator 154 can be configured to perform a multi-variable regression (e.g., perform a multi-variable polynomial curve fit, perform a multi-variable linear regression), use a neural network, or create a matrix/table to create a model that relates the parameters to known values of $V_{wound}$. In some embodiments, model generator 154 creates a model for a variety of values of $V_{system}$. For example, model generator 154 can create a table for each of a variety of typical values of $V_{system}$ which correspond to various NPWT circuits that may be used during NPWT.

Referring again to FIG. 5, controller 118 is shown to include a model generator 154, according to some embodiments. Model generator 154 can be configured to generate a model that defines a relationship between the parameters of the dynamic pressure response and the volume of wound 114. To generate the model, model generator 154 can cause testing procedure controller 148 to run the pressure testing procedure outlined above for several different training circuits having several different known volumes (e.g., 50 cc, 100 cc, 200 cc, 300 cc, etc.). When the pressure testing procedure is performed on a training circuit having a known volume, the pressure testing procedure may be referred to as a training procedure. Each performance of the training procedure may include applying the pressure stimulus to a training circuit having a known volume, observing the dynamic pressure response of the training circuit to the pressure stimulus (e.g., determining/measuring $\alpha_{leak}$ and $\alpha_{time}$), and associating the known volume with the dynamic pressure response of the training circuit.

In some embodiments, model generator 154 records the values of the parameters of the dynamic pressure response (i.e., the leak rate parameter $\alpha_{leak}$ and the drawdown time parameter $\alpha_{time}$) for each known volume and associates those values with the known volume. The values of the parameters and the known volume form a set of training data which can be used to construct the model. The values of the parameters form a set of model input training data, whereas the known volumes form a set of model output training data. Model generator 154 can use any of a variety of model generation techniques to construct a model (i.e., a mathematical model) that relates the values of the parameters to the corresponding volume in the set of training data.

In some embodiments, model generator 154 creates a n by m matrix A (i.e., a model) for each typical value of $V_{system}$ (i.e., typical negative pressure wound therapy systems). In some embodiments, the matrix A relates the leak rate parameter values $\alpha_{leak}$ and the drawdown time parameter values $\alpha_{drawdown}$ to the known wound volume values $V_{wound}$ associated with the parameters. In some embodiments, the matrix A has the form:

$$A = \begin{bmatrix} V_{1,1} & V_{1,2} & \cdots & V_{1,m} \\ V_{2,1} & V_{2,2} & \cdots & V_{2,m} \\ \cdots & \cdots & \cdots & \cdots \\ V_{n,1} & V_{n,2} & \cdots & V_{n,m} \end{bmatrix}$$

where each column represents volumes of wound 114 corresponding to a different value of the drawdown time parameter $\alpha_{time}$, each row represents different volumes of wound 114 corresponding to a different leak rate parameter $\alpha_{leak}$, and each element of the matrix represents a volume of $V_{wound}$ which corresponds to the particular combination of $\alpha_{time}$ and $\alpha_{leak}$. In some embodiments, model generator 154 is configured to receive various data sets where each data set includes a value of $V_{wound}$ for which the particular test was performed, and the values of $\alpha_{time}$ and $\alpha_{leak}$ that resulted from the test. In some embodiments, model generator 154 is configured to receive data sets from each iteration of the test and create matrix A based on the data sets. In some embodiments, matrix A is created (e.g., sorted, arranged, generated, constructed, etc.) such that the values of $\alpha_{time}$ (e.g., associated with the columns of matrix A) increase from left to right, and such that the values of $\alpha_{leak}$ (e.g., associated with the rows of matrix A) increase from top to bottom of matrix A.

In some embodiments, model generator 154 also generates vectors which correspond to the rows and columns of matrix A. In some embodiments, the vectors are row and column vectors of the drawdown time parameters $\alpha_{time}$ and the leak rate parameters $\alpha_{leak}$ which were determined through testing for the associated volume values. For example, the vector of the drawdown time parameters $\alpha_{time}$ may be referred to as vector C and have the form:

$$C = [\alpha_{time,1} \alpha_{time,2} \cdots \alpha_{time,m}]$$

according to some embodiments. Likewise, the vectors of the leak rate parameters $\alpha_{leak}$ may be referred to as vector B and have the form:

$$B = [\alpha_{leak,1} \alpha_{leak,2} \cdots \alpha_{leak,n}]^T$$

according to some embodiments.

In some embodiments, model generator 154 creates a table 900 as shown in FIG. 9 based on the datasets received from testing procedure controller 148. Table 900 includes a horizontal/top header 902 and a vertical/side header 904, according to some embodiments. In some embodiments, top header 902 represents various values of $\alpha_{time}$, and columns corresponding to various values of $V_{wound}$. Side header 904 represents various values of $\alpha_{leak}$ and rows correspond to various values of $V_{wound}$. In some embodiments, top header 902 and the corresponding columns of $V_{wound}$ values are sorted in an ascending order of $\alpha_{time}$, with lower values of $\alpha_{time}$ farther left and higher values of $\alpha_{time}$ farther right. Likewise, side header 904 is sorted in ascending order of $\alpha_{leak}$ with lower values of $\alpha_{leak}$ at the top of side header 904 and higher values of $\alpha_{leak}$ at the bottom of side header 904, according to some embodiments.

In some embodiments, model generator 154 performs a multi-variable regression based on the values of $V_{wound}$ and the corresponding $\alpha_{time}$ and $\alpha_{leak}$ parameters. In some embodiments, model generator 154 performs a multi-variable linear regression to determine the equation:

$$V_{wound} = C_1 \alpha_{time} + C_2 \alpha_{leak} + C_3$$

where $C_1$, $C_2$, and $C_3$ are constants determined by model generator 154 by performing the multi-variable linear regression.

In some embodiments, model generator 154 performs a multi-variable non-linear regression to determine the equation:

$$V_{wound} = f_1(\alpha_{time}) + f_2(\alpha_{leak})$$

where $f_1$ is a non-linear function of $\alpha_{time}$ determined by performing the non-linear multi variable regression, and $f_2$ is a non-linear function of $\alpha_{leak}$ determined by performing the non-linear multi variable regression. In some embodiments, any of the above equations have the general form:

$$V_{wound} = f_{wound}(\alpha_{time}, \alpha_{leak})$$

where $f_{wound}$ is a function (e.g., linear, non-linear, etc.) relating $\alpha_{leak}$ and $\alpha_{time}$ to $V_{wound}$. In some embodiments, $f_{wound}$ is determined by performing a multi-variable regression on the various values of $V_{wound}$ and the associated values of $\alpha_{time}$ and $\alpha_{leak}$ corresponding to each of the $V_{wound}$ values.

In some embodiments, model generator 154 creates $f_{wound}$ using a polynomial approximation model to relate the values of the parameters to the corresponding volume. To generate a polynomial approximation model, model generator 154 can perform a curve fitting process such as polynomial regression using any of a variety of regression techniques. Examples of regression techniques which can be used by model generator 154 include least squares, ordinary least squares, linear least squares, partial least squares, total least squares, generalized least squares, weighted least squares non-linear least squares, non-negative least squares, iteratively reweighted least squares, ridge regression, least absolute deviations, Bayesian linear regression, Bayesian multivariate linear regression, etc.

In some embodiments, $f_{wound}$ is generated by model generator 154 using a neural network. To generate a neural network model, model generator 154 can perform a machine learning process. Examples of machine learning techniques which can be used by model generator 154 include decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule-based machine learning, etc.

Referring still to FIG. 5, controller 118 is shown to include wound volume estimator 156, according to some embodiments. In some embodiments, wound volume estimator 156 is provided with any of matrix A and the associated vectors B and C, table 900, and/or the mathematical model determined by model generator 154 (e.g., $f_{wound}$). In some embodiments, wound volume estimator 156 is configured to cause testing procedure controller 148 to perform the testing procedure as described in greater detail above with reference to FIG. 6 for an unknown wound volume. In some embodiments, wound volume estimator 156 is configured to perform the testing procedure. For example, wound volume estimator 156 may be configured to perform any of the functionality of testing procedure controller 148 (e.g., to perform first drawdown period 604, operate valve 132, control pneumatic pump 120, etc.). In some embodiments, wound volume estimator 156 determines the values of $\alpha_{time}$ and $\alpha_{leak}$ or receives the determined values of $\alpha_{time}$ and $\alpha_{leak}$ from testing procedure controller 148. In some embodiments, wound volume estimator 156 uses any of the mathematical models (e.g., $f_{wound}$), matrix A, table 900, etc., generated and received from model generator 154 to determine an estimated value of the unknown value of $V_{wound}$. In some embodiments, if wound volume estimator 156 uses table 900 and/or matrix A, and one or both of the values of $\alpha_{time}$ and $\alpha_{leak}$ do not correspond to the values of $\alpha_{time}$ and $\alpha_{leak}$ as stored in vectors B and C or in table 900, wound volume estimator 156 is configured to perform an interpolation to determine $V_{wound}$.

In some embodiments, wound volume estimator 156 uses table 900 to determine the unknown value $V_{wound}$ based on the determined parameters $\alpha_{time}$ and $\alpha_{leak}$ resulting from performing the testing procedure on wound 114 with an unknown volume. In some embodiments, wound volume estimator 156 first checks through the values of side header 904 to determine if any of the values of $\alpha_{leak}$ in side header 904 are substantially equal to the value of $\alpha_{leak}$ determined from performing the testing procedure on wound 114 with the unknown value of $V_{wound}$. For example, if wound volume estimator 156 determines that $\alpha_{leak}$ is substantially equal to $\alpha_{leak,2}$ of side header 904, wound volume estimator 156 determines that the value of $V_{wound}$ is one of the values of V in the row corresponding to $\alpha_{leak,2}$. Next, wound volume estimator 156 can compare the various values of $\alpha_{time}$ in the top header 902 to the value of $\alpha_{time}$ determined from performing the testing procedure on wound 114. For example, if wound volume estimator 156 determines that $\alpha_{time}$ is substantially equal to $\alpha_{time,5}$, and $\alpha_{leak}$ is substantially equal to $\alpha_{leak,2}$, wound volume estimator 156 can determine that the volume of wound 114 is substantially equal to $V_{2,5}$.

In some embodiments, if wound volume estimator 156 determines that $\alpha_{leak}$ and/or $\alpha_{time}$ do not correspond to values of side header 904 and top header 902, respectively, wound volume estimator 156 can perform an interpolation or an extrapolation to determine the volume of wound 114. In some embodiments, wound volume estimator 156 uses any of the values of table 900 in a multi-variable linear interpolation (or extrapolation) to determine the volume of wound 114. In some embodiments, wound volume estimator 156 performs a non-linear interpolation to determine the volume of wound 114.

Wound volume estimator 156 can be similarly configured to determine the volume of wound 114 using matrix A and vectors B and C. For example, wound volume estimator 156 can compare the value of $\alpha_{time}$ to values of the elements of vector C to determine a column value of matrix A, and compare the value of $\alpha_{leak}$ to values of the elements of vector B to determine a row value of matrix A. For example, if $\alpha_{time}$ is equal to the fifth element of vector C and $\alpha_{leak}$ is equal to the tenth element of vector C, wound volume estimator 156 can select A(10,5) or $V_{10,5}$ as $V_{wound}$ for wound 114. Likewise, wound volume estimator 156 can be configured to interpolate or extrapolate values of matrix A to determine values of $V_{wound}$ that are associated with a value of $\alpha_{time}$ and/or $\alpha_{leak}$ not included in vector B and vector C. In some embodiments, wound volume estimator 156 is configured to use a linear multi-variable interpolation technique or a non-linear interpolation technique.

In some embodiments, wound volume estimator 156 is configured to use any of the linear regression equations (e.g., $V_{wound}=C_1\alpha_{time}+C_2\alpha_{leak}+C_3$), the non-linear regression equation (e.g., $V_{wound}=f_1(\alpha_{time})+f_2(\alpha_{leak})$), or any of the mathematical models (e.g., generally referred to as $V_{wound}=f_{wound}(\alpha_{time},\alpha_{leak})$) determined using any of the methods described in greater detail above (e.g., generated using a machine learning algorithm, using a polynomial curve-fit, using a linear regression, etc.) using the data received from testing procedure controller 148 for the known volumes. For example, wound volume estimator 156 can input the determined values of $\alpha_{leak}$ and $\alpha_{time}$ (e.g., the parameters resulting from performing the testing procedure on a wound 114 with an unknown volume) into $f_{wound}$ to determine the volume $V_{wound}$ of wound 114. In some embodiments, wound volume estimator 156 is configured to select an appropriate model (e.g., an appropriate table 900, an appropriate matrix A, an appropriate $f_{wound}$) based on a volume (e.g., $V_{system}$) of circuit which pneumatic pump 120 is configured to drawdown. For example, wound volume estimator 156 can select an appropriate $f_{wound}$ model generated from a testing procedure for a system having a similar volume from a database of various $f_{wound}$ models.

Advantageously, using both $\alpha_{time}$ and $\alpha_{leak}$ to determine $V_{wound}$ reduces inaccuracies or deviations in $\alpha_{time}$ due to air leaking into inner volume 160 of wound 114, according to some embodiments. For example, a wound application for a wound having volume $V_{wound}$ with a high leak rate (e.g., a high value of $\alpha_{leak}$) may have a higher value of $\alpha_{time}$ when compared to a wound with the same volume $V_{wound}$ but a lower leak rate (e.g., a lower value of $\alpha_{leak}$). By taking both $\alpha_{time}$ and $\alpha_{leak}$ into account, model generator 154 and wound volume estimator 156 can account for the degree of leakage for the particular wound and accurately determine $V_{wound}$, regardless of high or low leakage rates (e.g., high or low values of $\alpha_{leak}$).

Flow Diagrams

Referring now to FIGS. 10-11, a graph 1000 and process 1100 illustrating an application of the wound volume estimates are shown, according to an exemplary embodiment. Controller 118 can use the estimated wound volume to calculate a volume of instillation fluid 105 to deliver to wound 114 (step 1102). In some embodiments, controller 118 calculates the volume of instillation fluid 105 to deliver to wound 114 by multiplying the estimated wound volume by a fluid instillation factor. The fluid instillation factor may be less than one (i.e., between zero and one) such that the calculated volume of instillation fluid 105 is less than the volume of wound 114. In some embodiments, the fluid instillation factor is between approximately 0.2 and approximately 0.8. However, it is contemplated that the fluid instillation factor can have any value in various alternative embodiments.

In graph 1000, line 1002 represents the estimated volume of wound 114 as a function of time, whereas line 1004 represents the calculated volume of instillation fluid 105 to deliver to wound 114 over time. At time $t_1$, the estimated volume of wound 114 is $V_4$. The estimated wound volume $V_4$ at time $t_1$ can be multiplied by the fluid instillation factor F (e.g., F=0.8) to calculate the volume of instillation fluid 105 $V_3$ to deliver to wound 114 at time $t_1$ (i.e., $V_4*F=V_3$). As wound 114 heals, the estimated volume of wound 114 decreases and reaches a value of $V_2$ at time $t_2$. The estimated wound volume $V_2$ at time $t_2$ can be multiplied by the fluid instillation factor F to calculate the volume of instillation fluid 105 $V_1$ to deliver to wound 114 at time $t_2$ (i.e., $V_2*F=V_1$).

Controller 118 can then operate a pump to deliver the calculated volume of instillation fluid 105 to wound 114 (step 1104). Step 1104 can include operating instillation pump 122 to draw instillation fluid 105 from instillation fluid canister 104 and deliver instillation fluid 105 to wound 114 via tubing 109 and 108. In some embodiments, the calculated volume of instillation fluid 105 is also used to control the operation of pneumatic pump 120. For example, controller 118 can operate pneumatic pump 120 to remove the volume of instillation fluid 105 from wound 114 via tubing 110. The amount of time that pneumatic pump 120 operates may be a function of the volume of instillation fluid 105 that was delivered to wound 114.

Figure 12A:
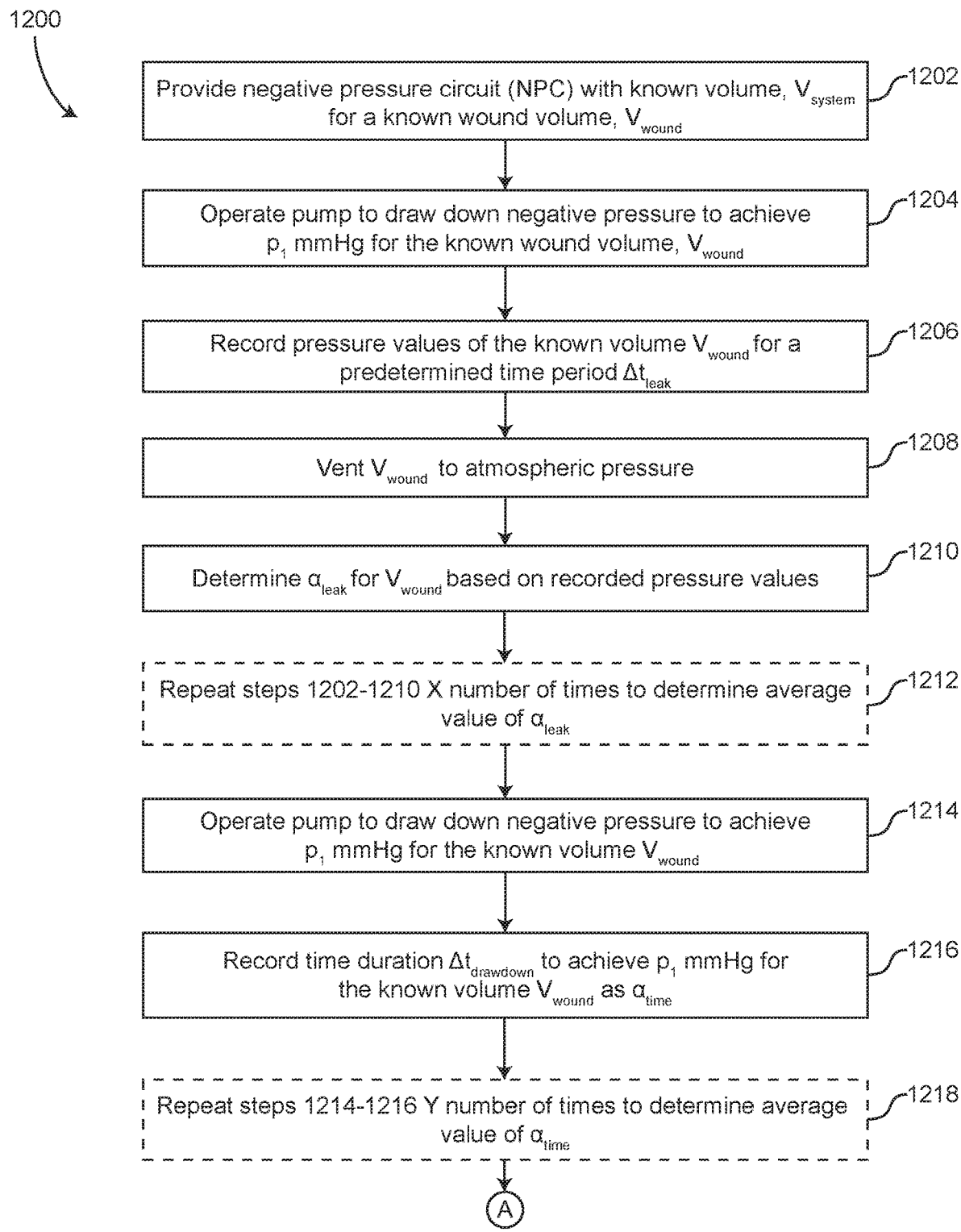
FIGS. 12A-B are a flowchart of a process for generating a model that relates drawdown time parameters and leak rate parameters to wound volume, according to an exemplary embodiment.
Figure 12B:
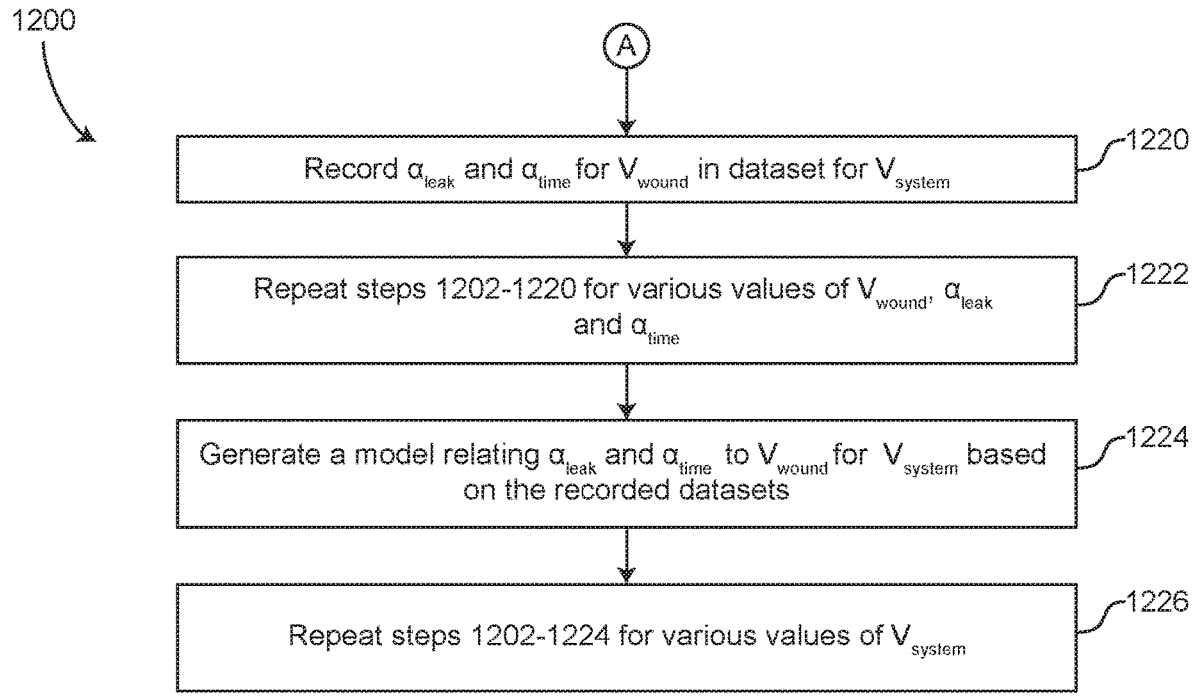

Referring now to FIGS. 12A-B, a process 1200 for generating a model (e.g., $f_{wound}$) to relate one or more parameters (e.g., $\alpha_{leak}$ and $\alpha_{time}$) to a wound volume (e.g., $V_{wound}$) is shown, according to some embodiments. In some embodiments, controller 118 is configured to perform process 1200. In some embodiments, process 1200 is performed by controller 118 and/or the various components of NPWT system 100. In some embodiments, process 1200 illustrates various steps that controller 118 can perform to determine $f_{wound}$. In some embodiments, process 1200 is the testing procedure described in greater detail above with reference to FIGS. 5-7. Process 1200 includes steps 1202-1226, according to some embodiments.

Process 1200 includes providing a negative pressure circuit (NPC) with a known volume $V_{system}$ for a known wound volume $V_{wound}$ (step 1202), according to some embodiments. In some embodiments, providing the NPC circuit for the known wound includes setting up a NPC circuit by providing wound dressing 112 to patient's skin 116 over wound 114. In some embodiments, $V_{wound}$ is a known volume of wound 114. For example, step 1202 may include configuring NPWT system 100 (e.g., having a known $V_{system}$) to perform NPWT for a test wound (e.g., wound 114 with a known volume $V_{wound}$). In some embodiments, step 1202 includes setting up NPWT system 100 and starting therapy device 102.

Process 1200 includes operating a pump to draw down negative pressure at wound 114 to achieve $p_1$ at the known wound volume $V_{wound}$ (step 1204), according to some embodiments. in some embodiments, step 1204 is first drawdown period 604. In some embodiments, the pump is pneumatic pump 120. In some embodiments, step 1204 includes any of the functionality, techniques, steps, etc., of first drawdown period 604. In some embodiments, step 1204 is performed by testing procedure controller 148. In some embodiments, $p_1$ is 200 mmHg. In some embodiments, step 1204 is performed by testing procedure controller 148 and pump controller 146. Pneumatic pump 120 is configured to produce a negative pressure at wound 114, according to some embodiments. In some embodiments, step 1204 includes testing procedure controller 148 monitoring pressure measurements at wound 114 via pressure sensors 130, 113, and continuing to cause pneumatic pump 120 to drawdown the negative pressure until the measured/monitored pressure is substantially equal to $p_1$. In some embodiments, step 1204 is also performed by valve controller. In some embodiments, step 1204 includes valve controller 150 sending a control signal to valve 132 to transition valve 132 into a closed configuration such pneumatic pump 120 can drawdown a negative pressure at wound 114.

Process 1200 includes recording pressure values of the known volume $V_{wound}$ for a predetermined time period $\Delta t_{leak}$ (step 1206), according to some embodiments. In some embodiments, step 1206 is leak rate determination period 606. In some embodiments, controller 118 is configured to perform step 1206. In some embodiments, step 1206 is performed by testing procedure controller 148. For example, testing procedure controller 148 can be configured to receive pressure measurements from pressure sensors 130/113 over time period $\Delta t_{leak}$ (e.g., $t_2-t_1$ as shown in FIG. 6) to perform step 1206. In some embodiments, step 1206 includes recording multiple pressure values of the negative pressure (e.g., vacuum pressures) of wound 114. In some embodiments, step 1206 includes recording an initial pressure value (e.g., $p_1$) of wound 114 at a beginning of time period $\Delta t_{leak}$, and a final pressure value (e.g., $p_2$) at an end of time period $\Delta t_{leak}$. In some embodiments, step 1206 is performed by testing procedure controller 148 and pressure monitor 152.

Process 1200 includes venting wound 114 to atmospheric pressure (step 1208), according to some embodiments. In some embodiments, step 1208 is performed after step 1210. In some embodiments, step 1208 and step 1210 are performed simultaneously. In some embodiments, step 1208 is performed by testing procedure controller 148 and valve controller 150. For example, step 1208 may include testing procedure controller 148 sending a command to valve controller 150 to transition valve 132 into the open configuration such that wound 114 can return to atmospheric pressure. In some embodiments, step 1208 is performed by testing procedure controller, valve controller 150, and valve 132. In some embodiments, step 1208 is vent period 608.

Process 1200 includes determining the leak rate parameter $\alpha_{leak}$ for $V_{wound}$ based on the pressure values of wound 114 recorded during step 1206 (step 1210), according to some embodiments. In some embodiments, step 1210 is performed by testing procedure controller 148. In some embodiments, $\alpha_{leak}$ is a difference between an initial pressure value and a final pressure value of time interval $\Delta t_{leak}$. In some embodiments, $\alpha_{leak}$ is slope 612. In some embodiments, $$\alpha_{leak} = \frac{s_w - s_1}{t_{s_w} - t_{s_1}} = \frac{p_2 - p_1}{t_2 - t_1}.$$

Process 1200 includes repeating steps 1202-1210 (step 1212), according to some embodiments. In some embodiments, controller 118 and/or NPWT system 100 repeat steps 1202-1210 X number of times to determine an average value of $\alpha_{leak}$ to minimize random error. In some embodiments, step 1212 is optional.

Process 1200 includes operating the pump (e.g., pneumatic pump 120) to draw down negative pressure at wound 114 to achieve $p_1$ (step 1214), according to some embodiments. In some embodiments, step 1214 is second drawdown period 610. In some embodiments, step 1214 is performed by testing procedure controller 148, pump controller 146, and pneumatic pump 120. In some embodiments, the pressure is drawn down to pressure $p_1$. In some embodiments, the pressure is drawn down to a pressure greater than or less than pressure $p_1$.

Process 1200 includes recording a time duration $\Delta t_{drawdown}$ to achieve $p_1$ for wound 114 as $\alpha_{time}$ (step 1216), according to some embodiments. In some embodiments, time duration $\Delta t_{drawdown}$ is time interval 614. In some embodiments, $\alpha_{time}$ is the amount of time that pneumatic pump 120 must operate to achieve pressure $p_1$. In some embodiments, step 1216 is performed by testing procedure controller 148.

Process 1200 includes repeating steps 1214-1216 Y number of times to determine an average value of $\alpha_{time}$ (step 1218), according to some embodiments. In some embodiments, steps 1214-1216 are repeated in order to reduce an amount of random error in $\alpha_{time}$. In some embodiments, step 1218 is optional.

Process 1200 includes recording the leak rate parameter $\alpha_{leak}$ and the drawdown time parameter $\alpha_{time}$ associated with the value of $V_{wound}$ in a dataset (step 1220), according to some embodiments. In some embodiments, step 1220 is performed by testing procedure controller 148. In some embodiments, step 1220 includes generating a matrix N=[$\alpha_{time}$ $\alpha_{leak}$ $V_{wound}$] and providing matrix N to model generator 154. In some embodiments, the matrix N is stored, and additional performances of steps 1202-1220 define additional rows for the matrix N.

Process 1200 includes repeating steps 1202-1220 for various values of $V_{wound}$, $\alpha_{leak}$, and $\alpha_{time}$ (step 1222), according to some embodiments. In some embodiments, each additional iteration of steps 1202-1220 results in an additional row of the matrix N. In some embodiments, steps 1202-1220 are performed until a sufficient amount of test data is recorded in matrix N. In some embodiments, steps 1202-1220 are performed for various values of $V_{wound}$ which are typical, and for various leakages $\alpha_{leak}$ that may be encountered during implementation of NPWT.

Process 1200 includes generating a model (e.g., $f_{wound}$) relating $V_{wound}$ to $\alpha_{leak}$ and $\alpha_{time}$ for a current value of $V_{system}$ (step 1224) based on the recorded datasets (e.g., matrix N), according to some embodiments. In some embodiments, step 1224 is performed by model generator 154. In some embodiments, step 1224 includes providing the recorded datasets (e.g., matrix N) to model generator 154. In some embodiments, the generated model is matrix A, table 900, $f_{wound}$, etc. In some embodiments, step 1224 includes performing any of a regression, a curve fitting technique, a machine learning algorithm, etc., to determine $f_{wound}$. In some embodiments, step 1224 includes arranging, sorting, etc., matrix N to generate matrix A or table 900. In some embodiments, a model is generated for each of multiple values of $V_{system}$. In some embodiments, step 1224 includes providing the generated model to wound volume estimator 156.

Process 1200 includes repeating steps 1202-1224 for various values of $V_{system}$ (step 1226) to determine models that relate $\alpha_{leak}$ and $\alpha_{time}$ to $V_{wound}$ for each of the various values of $V_{system}$, according to some embodiments. In some embodiments, step 1226 includes performing steps 1204-1224 for various NPWT systems. In some embodiments, step 1226 is performed by controller 118 and a test technician (e.g., step 1202 may include replacing a current NPWT system with a different system having a different $V_{system}$).

Figure 13:
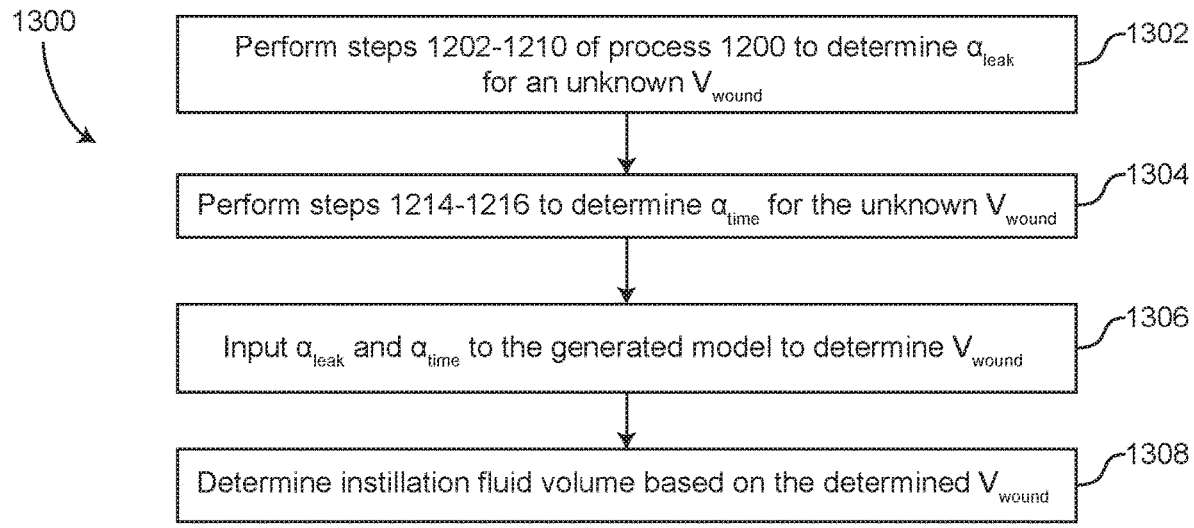
FIG. 13 is a flowchart of a process for determining wound volume and instillation volume, according to an exemplary embodiment.

Referring now to FIG. 13, a process 1300 for determining the volume $V_{wound}$ of wound 114 (i.e., if the volume of wound 114 is unknown) is shown, according to some embodiments. Process 1300 may rely on the model(s) generated in process 1200 by model generator 154. In some embodiments, process 1300 can be performed intermittently throughout NPWT to determine the volume of wound 114. Process 1300 can be performed by controller 118. Process 1300 includes steps 1302-1308, according to some embodiments.

Process 1300 includes performing steps 1202-1210 of process 1200 to determine the leak rate parameter $\alpha_{leak}$ for an unknown value of $V_{wound}$ (step 1302), according to some embodiments. In some embodiments, step 1302 is performed by controller 118.

Process 1300 includes performing steps 1214-1216 to determine the drawdown time parameter $\alpha_{time}$ (step 1304) for the unknown value of $V_{wound}$ (step 1304), according to some embodiments. In some embodiments, step 1304 is performed by controller 118.

Process 1300 includes inputting $\alpha_{leak}$ and $\alpha_{time}$ to the model generated by model generator 154 in process 1200 (step 1306), according to some embodiments. In some embodiments, step 1306 includes inputting $\alpha_{leak}$ and $\alpha_{time}$ into $f_{wound}$ for a present NPWT system having $V_{system}$ to determine $V_{wound}$. In some embodiments, step 1306 is performed by wound volume estimator 156. In some embodiments, step 1306 includes looking up a value of $V_{wound}$ in table 900 and/or matrix A based on $\alpha_{leak}$ and $\alpha_{time}$. In some embodiments, step 1306 includes interpolating or extrapolating to determine the value of $V_{wound}$ if $\alpha_{leak}$ does not match any of the values of side header 904 and/or vector B, or if $\alpha_{time}$ does not match any of the values of top header 902 and/or vector C.

Process 1300 includes determining an instillation fluid volume based on the determine $V_{wound}$ of step 1306 (step 1308), according to some embodiments. In some embodiments, step 1308 is performed by controller 118. In some embodiments, step 1308 is step 1101 of process 1100.

Figure 14:
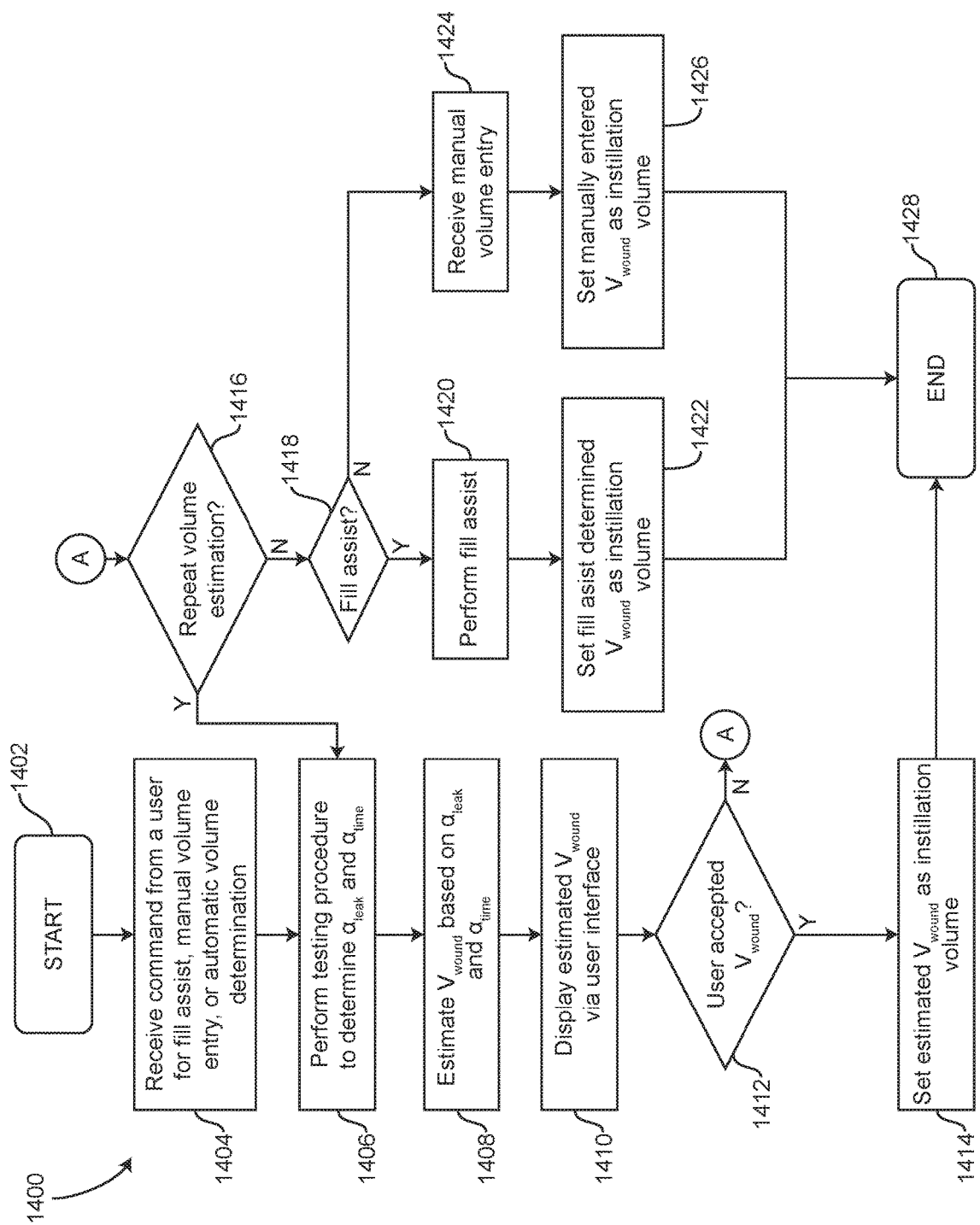
FIG. 14 is a flowchart of a process of operating the therapy device of FIG. 1, according to an exemplary embodiment.

Referring now to FIG. 14, process 1400 for operating therapy device 102 is shown, according to some embodiments. Process 1400 can be performed by controller 118, communications interface 124, and user interface 126. In some embodiments, process 1400 is a process for determining a volume of a wound (e.g., wound 114).

Process 1400 initiates with startup of therapy device 102 (step 1402), according to some embodiments. In some embodiments, after therapy device 102 has started, process 1200 proceeds to step 1404. At step 1404, controller 118 can receive a command from a user to transition therapy device 102 into fill assist mode, manual volume move, or automatic volume determination mode. In some embodiments, the command is received via user interface 126. If the user sends a command to transition therapy device 102 into the fill assist mode, therapy device 102 transitions into the fill assist mode, and process 1400 proceeds to step 1420, according to some embodiments. If the user sends a command to transition therapy device 102 into the manual volume entry mode, process 1400 proceeds to step 1426, according to some embodiments. If the user sends a command to transition therapy device 102 into an automatic volume detection mode, process 1400 proceeds to step 1406, according to some embodiments.

Process 1400 includes performing the testing procedure to determine the leak rate parameter $\alpha_{leak}$ and the drawdown time parameter $\alpha_{time}$ (step 1406), according to some embodiments. In some embodiments, the testing procedure is the testing procedure described in greater detail above with reference to FIG. 6. In some embodiments, the testing procedure is process 1300. In some embodiments, step 1406 is performed by controller 118 and/or testing procedure controller 148.

Process 1400 includes estimating $V_{wound}$ based on the leak rate parameter $\alpha_{leak}$ and the drawdown time parameter $\alpha_{time}$ (step 1408), according to some embodiments. In some embodiments, step 1408 is performed by wound volume estimator 156 using the model generated by model generator 154. In some embodiments, the model $f_{wound}$, or table 900, or matrix A (and vectors B and C) are preloaded into memory 144 of controller 118 for a variety of values of $V_{system}$. In some embodiments, step 1408 is step 1306 of process 1300. In some embodiments, step 1408 includes inputting the leak rate parameter $\alpha_{leak}$ and the drawdown time parameter $\alpha_{time}$ into the model (as generated by model generator 154, described in greater detail above) to determine $V_{wound}$.

Process 1400 includes displaying the value of $V_{wound}$ determined in step 1408 via user interface 126 (step 1410), according to some embodiments. In some embodiments, the value of $V_{wound}$ is displayed via user interface 126 in response to completing step 1408. In some embodiments, the value of $V_{wound}$ is displayed via user interface 126 in addition to a confirmation from the user to accept or reject the value of $V_{wound}$.

Process 1400 includes determining (e.g., receiving an input) whether the user has accepted the value of $V_{wound}$ as determined in step 1408 (step 1412), according to some embodiments. In some embodiments, a request is displayed via user interface 126 requesting confirmation of the value of $V_{wound}$. In some embodiments, controller 118 receives a command from a user (e.g., a yes or a no command) indicating whether the user has accepted the value of $V_{wound}$. If controller 118 receives a command from the user indicating that the user has accepted the value of $V_{wound}$ (YES), process 1400 proceeds to step 1414, according to some embodiments. If controller 118 receives a command from the user indicating that the user has rejected the value of $V_{wound}$ (NO), process 1400 proceeds to step 1416.

Process 1400 includes setting the value of $V_{wound}$ equal to the instillation volume (step 1414), according to some embodiments. In some embodiments, step 1414 is performed by controller 118. In some embodiments, step 1414 includes determining the instillation volume (e.g., a volume of instillation fluid 105 to be provided to wound 114) based on the value of $V_{wound}$. In some embodiments, step 1414 includes performing process 1100. In some embodiments, process 1400 ends (step 1428) in response to completing step 1414.

If controller 118 receives a command via user interface 126 that the user has rejected the value of $V_{wound}$ (NO, step 1412), process 1400 proceeds to step 1416, according to some embodiments. In some embodiments, step 1416 includes requesting an input from the user via user interface 126 whether the automatic volume estimation (i.e., steps 1406-1410) should be performed again. In some embodiments, if controller 118 receives a command from the user via user interface 126 to re-perform the automatic volume estimation, process 1400 returns to step 1406. If controller 118 receives a command from the user via user interface 126 that indicates the automatic volume estimation should not be performed again, process 1400 proceeds to step 1418, according to some embodiments.

Process 1400 includes requesting an input from a user whether or not to transition into the fill assist mode (step 1418), according to some embodiments. In some embodiments, step 1418 includes providing a request to the user via user interface 126. In some embodiments, if controller 118 receives a command from the user via user interface 126 to perform the fill assist (YES, step 1418), process 1400 proceeds to step 1420. In some embodiments, if controller 118 receives a command from the user via user interface 126 that a fill assist operation should not be performed (NO, step 1418), process 1400 proceeds to step 1424.

Process 1400 includes performing a fill assist operation (step 1420), according to some embodiments. In some embodiments, the fill assist operation is performed by controller 118 and instillation pump 122. In some embodiments, the fill assist operation includes allowing a user to manually indicate an amount of instillation fluid 105 that should be provided to wound 114 by manually operating instillation pump 122. Controller 118 can be configured to measure a quantity of instillation fluid 105 added to wound 114 by instillation pump 122 during the fill assist operation (as controlled by the user), and can determine $V_{wound}$ based on the quantity of instillation fluid added to wound 114 during the fill assist operation (step 1422). In some embodiments, in response to completing the fill assist operation, process 1400 proceeds to step 1428.

If controller 118 receives a command via user interface 126 that the fill assist operation should not be performed (step 1418, NO), process 1400 proceeds to step 1424, according to some embodiments. At step 1424, controller 118 receives a manual volume entry via user interface 126, according to some embodiments. In some embodiments, in response to receiving the manual volume entry via user interface 126, process 1400 proceeds to step 1426. At step 1426, controller 118 sets the manually entered volume (e.g., manually entered $V_{wound}$) as the instillation fluid volume. In some embodiments, after the manually entered volume has been set as the instillation fluid volume, process 1400 proceeds to step 1428.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

The invention claimed is:

1. A wound therapy device comprising:
a pump fluidly coupled to a negative pressure circuit and configured to produce a negative pressure at a wound or within the negative pressure circuit, wherein the negative pressure circuit is configured to apply negative pressure to the wound;
a pressure sensor configured to measure the negative pressure within a negative pressure circuit or at the wound; and
a controller configured to:
operate the pump to produce a negative pressure within the negative pressure circuit;
receive one or more pressure measurements of the pressure sensor over a predetermined time period;
determine a leakage rate based on the one or more received pressure measurements of the pressure sensor over the predetermined time period;
vent the negative pressure circuit to atmospheric pressure;
operate the pump to decrease the negative pressure within the negative pressure circuit at a predetermined rate;
monitor an amount of elapsed time that the pump operates at the predetermined rate until a predetermined pressure is achieved within the negative pressure circuit; and
estimate a volume of the wound based on the leakage rate and the amount of elapsed time.

2. The wound therapy device of claim 1, wherein the wound therapy device further comprises a vent configured to close while the pump produces a negative pressure within the negative pressure circuit.

3. The wound therapy device of claim 2, wherein the vent remains closed while the controller determines the leakage rate based on the one or more received pressure measurements of the pressure sensor over the predetermined time period.

4. The wound therapy device of claim 2, wherein the controller is configured to open the vent to vent the negative pressure circuit to atmospheric pressure.

5. The wound therapy device of claim 2, wherein the vent is configured to close while the pump is decreasing the negative pressure within the negative pressure circuit at a predetermined rate.

6. The wound therapy device of claim 1, wherein the controller is configured to operate the pump to produce the negative pressure within the negative pressure circuit at a maximum drawdown rate.

7. A wound therapy system having a negative pressure circuit configured to apply negative pressure to a wound and a pressure sensor configured to measure a pressure within the negative pressure circuit, the wound therapy system comprising:
a controller configured to:
perform a testing procedure comprising a first drawdown period, a leak rate determination period, a vent period, and a second drawdown period;
receive one or more pressure measurements of the pressure sensor over the leak rate determination period to determine a leak rate parameter;
monitor an amount of elapsed time over the second drawdown period to determine a drawdown parameter; and
estimate a volume of the wound based on the leak rate parameter and the drawdown parameter.

8. The wound therapy system of claim 7, further comprising a pump configured to be fluidly coupled to the negative pressure circuit and configured to produce a negative pressure at the wound or within the negative pressure circuit.

9. The wound therapy system of claim 8, wherein the first drawdown period comprises operating the pump to achieve a predetermined negative pressure within the negative pressure circuit.

10. The wound therapy system of claim 9, wherein the leak rate determination period comprises maintaining the predetermined negative pressure for a predetermined time duration and receiving pressure measurements from the pressure sensor during the predetermined time duration.

11. The wound therapy system of claim 8, wherein the second drawdown period comprises operating the pump to produce a negative pressure within the negative pressure circuit at a predetermined rate.

12. The wound therapy system of claim 7, wherein the vent period comprises opening a valve of the negative pressure circuit to allow the negative pressure circuit to return to atmospheric pressure.

13. The wound therapy system of claim 7, wherein the controller is further configured to estimate the volume of the wound by inputting the drawdown parameter and the leak rate parameter into a model that relates the volume of the wound to the drawdown parameter and the leak rate parameter.

\* \* \* \* \*